US012453605B2

(12) United States Patent
Malackowski et al.

(10) Patent No.: US 12,453,605 B2
(45) **Date of Patent: *Oct. 28, 2025**

(54) NAVIGATION SYSTEMS AND METHODS FOR REDUCING TRACKING INTERRUPTIONS DURING A SURGICAL PROCEDURE

(71) Applicant: MAKO Surgical Corp., Weston, FL (US)

(72) Inventors: Donald W. Malackowski, Schoolcraft, MI (US); José Luis Moctezuma de la Barrera, Freiburg (DE)

(73) Assignee: MAKO Surgical Corp., Weston, FL (US)

(*) Notice: Subject to any disclaimer, the term of this patent is extended or adjusted under 35 U.S.C. 154(b) by 332 days.

This patent is subject to a terminal disclaimer.

(21) Appl. No.: 17/982,845

(22) Filed: Nov. 8, 2022

(65) Prior Publication Data

US 2023/0053668 A1 Feb. 23, 2023

Related U.S. Application Data

(63) Continuation of application No. 16/853,146, filed on Apr. 20, 2020, now Pat. No. 11,517,377, which is a (Continued)

(51) Int. Cl.
*A61B 34/20* (2016.01)

(52) U.S. Cl.
CPC ...... *A61B 34/20* (2016.02); *A61B 2034/2055* (2016.02)

(58) Field of Classification Search
CPC . A61B 34/20; A61B 2034/2055; A61B 34/30; A61B 34/76; A61B 34/70
See application file for complete search history.

(56) References Cited

U.S. PATENT DOCUMENTS 5,430,643 A 7/1995 Seraji
5,548,694 A 8/1996 Frisken Gibson
(Continued)

FOREIGN PATENT DOCUMENTS

JP 2004223128 A 8/2004
JP 2006244046 A 9/2006
(Continued)

OTHER PUBLICATIONS

English language abstract and machine-assisted English translation for JP 2004-223128 A extracted from espacenet.com database on Aug. 4, 2021, 18 pages.
(Continued)

*Primary Examiner* — Joel Lamprecht
(74) *Attorney, Agent, or Firm* — Howard & Howard Attorneys PLLC

(57) ABSTRACT

Systems and methods are disclosed involving a navigation system including a localizer and a tracker detected within a field-of-view of the localizer. In one example, a virtual line-of-sight boundary is generated based on a line-of-sight relationship between the tracker and localizer. Additionally, or alternatively, a virtual field-of-view boundary is generated based on the field-of-view of the localizer. A virtual object is associated with a physical object and/or the tracker. Controller(s) detect whether a virtual collision occurs between the virtual object and the virtual line-of-sight boundary and/or virtual field-of-view boundary. The controller(s) enable a response based on detecting the virtual collision.

24 Claims, 9 Drawing Sheets

Related U.S. Application Data continuation of application No. 15/052,323, filed on Feb. 24, 2016, now Pat. No. 10,660,711.

(60) Provisional application No. 62/120,585, filed on Feb. 25, 2015.

(56) References Cited

U.S. PATENT DOCUMENTS

| | | | |
|---|---|---|---|
| 6,161,033 | A | 12/2000 | Kuhn |
| 6,671,581 | B2 | 12/2003 | Niemeyer et al. |
| 6,926,709 | B2 | 8/2005 | Bieger et al. |
| 7,663,629 | B2 | 2/2010 | Ajioka et al. |
| 7,725,162 | B2 | 5/2010 | Malackowski et al. |
| 8,010,180 | B2 | 8/2011 | Quaid et al. |
| 8,548,779 | B2 | 10/2013 | Ortmaier et al. |
| 8,774,969 | B2 | 7/2014 | Schreiber |
| 9,008,757 | B2 | 4/2015 | Wu |
| 9,119,655 | B2 | 9/2015 | Bowling et al. |
| 9,295,525 | B2 | 3/2016 | Hingwe et al. |
| 9,333,044 | B2 | 5/2016 | Olson |
| 9,381,085 | B2 | 7/2016 | Axelson, Jr. et al. |
| 9,492,235 | B2 | 11/2016 | Hourtash et al. |
| 9,566,120 | B2 | 2/2017 | Malackowski et al. |
| 9,694,497 | B2 | 7/2017 | Burmeister et al. |
| 9,717,461 | B2 | 8/2017 | Yu et al. |
| 9,718,190 | B2 | 8/2017 | Larkin et al. |
| 9,999,975 | B2 | 6/2018 | Frensch et al. |
| 10,350,012 | B2 | 7/2019 | Kang et al. |
| 10,660,711 | B2 | 5/2020 | Moctezuma de la Barrera et al. |
| 11,517,377 | B2 * | 12/2022 | Malackowski ........ A61B 34/76 |
| 2002/0087101 | A1 | 7/2002 | Barrick et al. |
| 2005/0273199 | A1 | 12/2005 | Ban et al. |
| 2006/0142657 | A1 | 6/2006 | Quaid et al. |
| 2007/0018958 | A1 | 1/2007 | Tavakoli et al. |
| 2009/0055024 | A1 | 2/2009 | Kay |
| 2010/0299101 | A1 | 11/2010 | Shimada et al. |
| 2011/0066282 | A1 | 3/2011 | Bosscher et al. |
| 2011/0263971 | A1 | 10/2011 | Nikou et al. |
| 2012/0330429 | A1 | 12/2012 | Axelson, Jr. et al. |
| 2013/0060278 | A1 | 3/2013 | Bozung et al. |
| 2013/0325029 | A1 | 12/2013 | Hourtash et al. |
| 2013/0331644 | A1 | 12/2013 | Pandya et al. |
| 2013/0345718 | A1 | 12/2013 | Crawford et al. |
| 2014/0039520 | A1 | 2/2014 | Haider et al. |
| 2014/0094968 | A1 | 4/2014 | Taylor et al. |
| 2014/0188132 | A1 | 7/2014 | Kang |
| 2014/0200621 | A1 | 7/2014 | Malackowski et al. |
| 2014/0276943 | A1 | 9/2014 | Bowling et al. |
| 2014/0288710 | A1 | 9/2014 | Ikenaga et al. |
| 2015/0297177 | A1 | 10/2015 | Boctor et al. |
| 2016/0000516 | A1 | 1/2016 | Cheng et al. |
| 2016/0242858 | A1 | 8/2016 | Moctezuma de la Barrera et al. |
| 2016/0345929 | A1 | 12/2016 | Azizian et al. |
| 2017/0143429 | A1 | 5/2017 | Richmond et al. |
| 2017/0245945 | A1 | 8/2017 | Zuhars et al. |
| 2017/0245946 | A1 | 8/2017 | Tabandeh et al. |
| 2018/0033385 | A1 | 2/2018 | Wang et al. |
| 2018/0235565 | A1 | 8/2018 | Azizian et al. |
| 2018/0235715 | A1 | 8/2018 | Amiot et al. |
| 2019/0054620 | A1 | 2/2019 | Griffiths et al. |
| 2019/0328479 | A1 | 10/2019 | Wada et al. |
| 2020/0246082 | A1 | 8/2020 | Malackowski et al. |

FOREIGN PATENT DOCUMENTS

| | | | |
|---|---|---|---|
| JP | 2006296760 | A | 11/2006 |
| JP | 2009537229 | A | 10/2009 |
| JP | 2013524952 | A | 6/2013 |
| WO | 2008031664 | A1 | 3/2008 |
| WO | 2011041428 | A2 | 4/2011 |
| WO | 2011134083 | A1 | 11/2011 |
| WO | 2014139022 | A1 | 9/2014 |
| WO | 2015120008 | A1 | 8/2015 |
| WO | 2018054729 | A1 | 3/2018 |
| WO | 2019134743 | A1 | 7/2019 |
| WO | 2020015836 | A1 | 1/2020 |

OTHER PUBLICATIONS

English language abstract and translation for JP 2006296760 extracted from espacenet.com database Jun. 22, 2016, 23 pages.

English language abstract for JP 2006-244046 A extracted from espacenet.com database on Aug. 4, 2021, 2 pages.

English language abstract for JP 2009-537229 extracted from espacenet.com database on Dec. 18, 2019, 2 pages.

English language abstract for JP 2013-524952 extracted from espacenet.com database on Dec. 18, 2019, 1 page.

English language abstract for WO 2018/054729 extracted from espacenet.com database on May 27, 2020, 2 pages.

International Search Report for Application No. PCT/US2016/019347 dated Jun. 15, 2016, 11 pages.

Jean-Christophe Lombardo et al., "Real-time Collision Detection for Virtual Surgery", HAL archives-ouvertes, Computer Animation, May 1999, IEEE Computer Society, pp. 82-90, Geneva, Switzerland.

Kenneth Salisbury et al., "Haptic Rendering: Introductory Concepts", IEEE Computer Society, Mar./Apr. 2004, pp. 24-32.

Ming C. Lin et al., "Collision detection between geometric models: a survey", University of North Carolina,1998 pp. 1-20.

* cited by examiner

NAVIGATION SYSTEMS AND METHODS FOR REDUCING TRACKING INTERRUPTIONS DURING A SURGICAL PROCEDURE

CROSS-REFERENCE TO RELATED APPLICATIONS

This application is a continuation of U.S. patent application Ser. No. 16/853,146, filed on Apr. 20, 2020, which is a continuation of U.S. patent application Ser. No. 15/052,323, filed Feb. 24, 2016, issued as U.S. Pat. No. 10,660,711, which claims priority to and the benefit of U.S. Provisional Patent App. No. 62/120,585, filed on Feb. 25, 2015, the entire contents of each of the aforementioned applications being incorporated by reference herein.

TECHNICAL FIELD

The disclosure relates generally to systems and methods for reducing tracking interruptions during a surgical procedure.

BACKGROUND

Navigation systems assist users in locating objects. For instance, navigation systems are used in industrial, aerospace, and medical applications. In the medical field, navigation systems assist surgeons in placing surgical tools relative to a patient's anatomy. Surgeries in which navigation systems are used include neurosurgery and orthopedic surgery. Typically, the tool and the anatomy are tracked together with their relative movement shown on a display.

Navigation systems may employ light signals, sound waves, magnetic fields, radio frequency signals, etc. in order to track the position and/or orientation of objects. Often the navigation system includes tracking devices attached to the object being tracked. A localizer cooperates with tracking elements on the tracking devices to determine a position of the tracking devices, and ultimately to determine a position and/or orientation of the object. The navigation system monitors movement of the objects via the tracking devices.

Many navigation systems rely on an unobstructed line-of-sight between the tracking elements and sensors of the localizer that receive tracking signals from the tracking elements. These navigation systems also rely on the tracking elements being positioned within a field-of-view of the localizer. As a result, efforts have been undertaken to reduce the likelihood of obstructing the line-of-sight between the tracking elements and the sensors and to maintain the tracking elements within the field-of-view of the localizer. For example, in some navigation systems, during initial setup of the navigation system, a display graphically represents a field-of-view of the localizer to guide initial placement of the tracking devices so that the tracking elements are located in the field-of-view free from obstructions to the line-of-sight. However, such navigation systems are unable to prevent obstructions to the line-of-sight that may arise during the surgical procedure as a result of the movement of objects into the line-of-sight, e.g., after the initial setup and during treatment of a patient, or to prevent the tracking elements from moving outside of the field-of-view.

When the line-of-sight is obstructed, or when the tracking elements are outside the field-of-view, tracking signals being transmitted from the tracking elements are not received by the localizer. As a result, errors can occur. Typically, in this situation, navigation is discontinued and error messages are conveyed to the user until the tracking signals are again received or the navigation system is reset. This can cause delays in surgical procedures. For instance, manipulators that rely on navigation data to autonomously position a cutting tool relative to the patient's tissue must cease operation should these errors occur. This could significantly increase the surgical procedure time, particularly if difficulty arises in restoring the line-of-sight. This is contrary to the demands of modern medical practice that require reduced surgery times in order to reduce risks of infection and risks associated with prolonged use of anesthesia.

Thus, there is a need in the art for navigation systems and methods that reduce tracking interruptions between tracking devices and a localizer receiving signals from the tracking devices so that surgical procedures are uninterrupted.

SUMMARY

According to a first aspect, a method is provided of operating a surgical system comprising a navigation system including a localizer including a field-of-view and a tracker, and one or more controllers coupled to the navigation system, the method comprising the one or more controllers: detecting the tracker within the field-of-view of the localizer by establishing a line-of-sight relationship between the tracker and the localizer; generating a virtual line-of-sight boundary based on the line-of-sight relationship; associating a virtual object with a physical object; detecting a virtual collision between the virtual object and the virtual line-of-sight boundary; and enabling a response based on detecting the virtual collision.

According to a second aspect, a method is provided of operating a surgical system comprising a navigation system including a localizer including a field-of-view and a tracker, and one or more controllers coupled to the navigation system, the method comprising the one or more controllers: detecting the tracker within the field-of-view of the localizer; generating a virtual field-of-view boundary based on the field-of-view of the localizer; associating a virtual object with the tracker; detecting a virtual collision between the virtual object and the virtual field-of-view boundary; and enabling a response based on detecting the virtual collision.

According to a third aspect, a surgical system is provided comprising: a navigation system including a localizer including a field-of-view and a tracker; and one or more controllers coupled to the navigation system, wherein the one or more controllers are configured to: detect the tracker within the field-of-view of the localizer with a line-of-sight relationship between the tracker and the localizer; generate a virtual line-of-sight boundary based on the line-of-sight relationship; associate a virtual object with a physical object; detect a virtual collision between the virtual object and the virtual line-of-sight boundary; and enable a response based on detection of the virtual collision.

According to a fourth aspect, a surgical system is provided comprising: a navigation system including a localizer including a field-of-view and a tracker; and one or more controllers coupled to the navigation system, wherein the one or more controllers are configured to: detect the tracker within the field-of-view of the localizer; generate a virtual field-of-view boundary based on the field-of-view of the localizer; associate a virtual object with the tracker; detect a virtual collision between the virtual object and the virtual field-of-view boundary; and enable a response based on detection of the virtual collision.

Advantages of these systems and methods include to reduce tracking interruptions between a tracking device and a localizer receiving signals from the tracking device so that interruptions to a surgical procedure can be avoided. Such interruptions can be caused by the manipulator and/or surgical tool interfering with the line-of-sight between the tracking device and the localizer and/or by virtue of the tracking device of the manipulator and/or surgical tool moving outside the field-of-view of the localizer.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
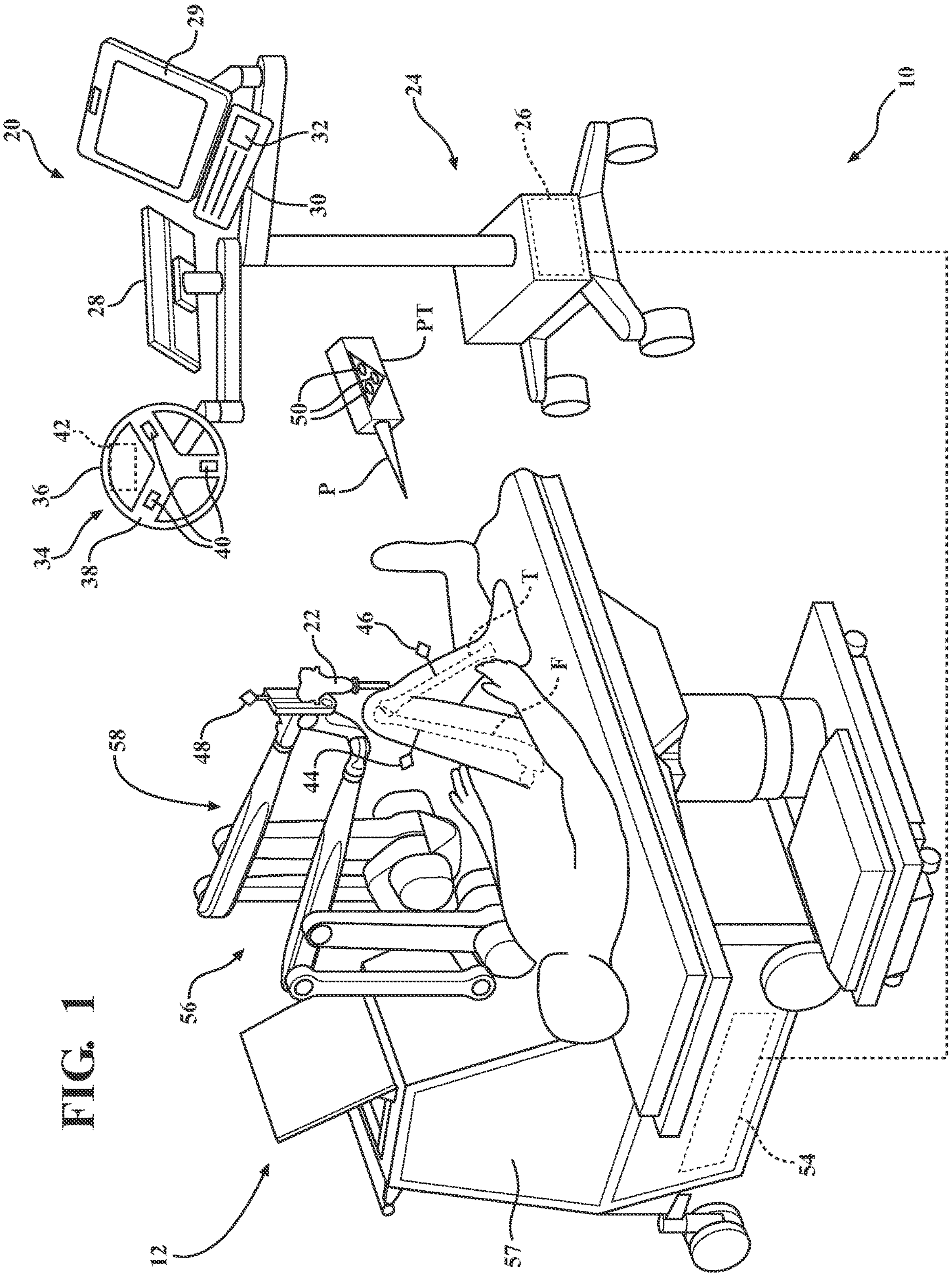
FIG. 1 is a perspective view of a material removal system being used to remove material from a workpiece.

Referring to FIG. 1 a material removal system 10 for removing material from a workpiece is illustrated. The material removal system 10 is shown in a surgical setting such as an operating room of a medical facility. In the embodiment shown, the material removal system 10 includes a machining station 12 and a navigation system 20. The navigation system 20 is set up to track movement of various objects in the operating room. Such objects include, for example, a surgical tool 22, a femur F of a patient, and a tibia T of the patient. The navigation system 20 tracks these objects for purposes of displaying their relative positions and orientations to the surgeon and, in some cases, for purposes of controlling or constraining movement of the surgical tool 22 relative to virtual cutting boundaries (not shown) associated with the femur F and tibia T.

The navigation system 20 includes a computer cart assembly 24 that houses a navigation computer 26. A navigation interface is in operative communication with the navigation computer 26. The navigation interface includes a first display 28 adapted to be situated outside of a sterile field and a second display 29 adapted to be situated inside the sterile field. The displays 28, 29 are adjustably mounted to the computer cart assembly 24. First and second input devices 30, 32 such as a keyboard and mouse can be used to input information into the navigation computer 26 or otherwise select/control certain aspects of the navigation computer 26. Other input devices are contemplated including a touch screen (not shown) or voice-activation.

A localizer 34 communicates with the navigation computer 26. In the embodiment shown, the localizer 34 is an optical localizer and includes a camera unit 36. The camera unit 36 has an outer casing 38 that houses one or more optical position sensors 40. In some embodiments at least two optical sensors 40 are employed, preferably three or four (three shown). The optical sensors 40 may be separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field-of-view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," hereby incorporated by reference.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Navigation system 20 is operable with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. patent application Ser. No. 14/156,856, filed on Jan. 16, 2014, entitled, "Navigation Systems and Methods for Indicating and Reducing Line-of-Sight Errors," hereby incorporated by reference herein. In additional embodiments, a tracker (not shown) is attached to the patella to track a position and orientation of the patella. In yet further embodiments, the trackers 44, 46 could be mounted to other tissue types or parts of the anatomy.

A tool tracker 48 is firmly attached to the surgical tool 22. The tool tracker 48 may be integrated into the surgical tool 22 during manufacture or may be separately mounted to the surgical tool 22 in preparation for surgical procedures. The working end of the surgical tool 22, which is being tracked by virtue of the tool tracker 48, may be a rotating bur, electrical ablation device, or the like.

The trackers 44, 46, 48 can be battery powered with an internal battery or may have leads to receive power through the navigation computer 26, which, like the camera unit 36, preferably receives external power.

In the embodiment shown, the surgical tool 22 is attached to a manipulator 56 of the machining station 12. Such an arrangement is shown in U.S. Pat. No. 9,119,655, entitled, "Surgical Manipulator Capable of Controlling a Surgical Instrument in Multiple Modes," the disclosure of which is hereby incorporated by reference.

Figure 2:
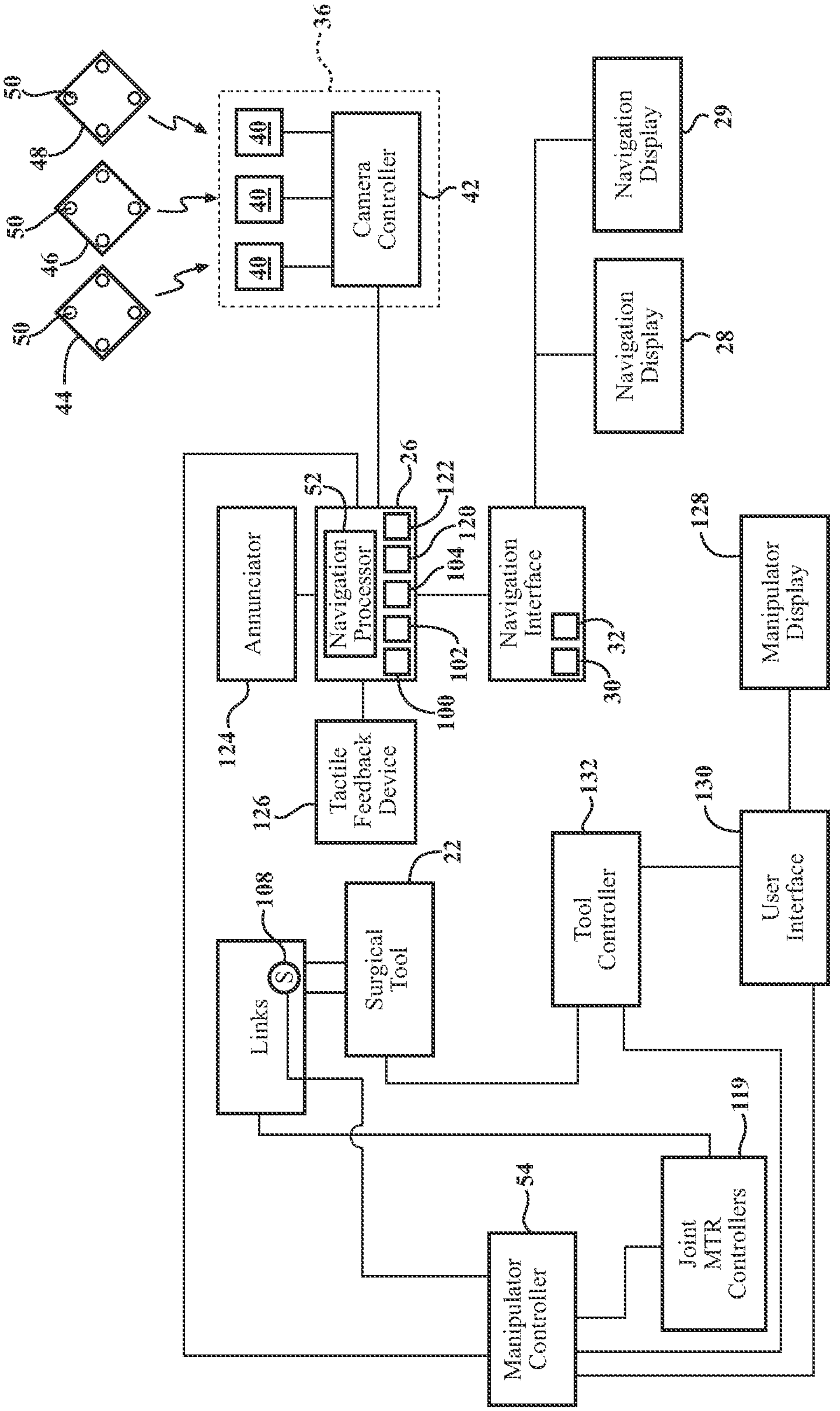
FIG. 2 is a schematic view of the material removal system.

Referring to FIG. 2, the optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Each of the LEDs 50 is connected to a tracker controller (not shown) located in a housing of the associated tracker 44, 46, 48 that transmits/receives data to/from the navigation computer 26. In one embodiment, the tracker controllers transmit data on the order of several Megabytes/second through wired connections with the navigation computer 26. In other embodiments, a wireless connection may be used. In these embodiments, the navigation computer 26 has a transceiver (not shown) to receive the data from the tracker controller.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor and accelerometer, such as the trackers shown in U.S. Pat. No. 9,008,757, filed on Sep. 24, 2013, entitled, "Navigation System Including Optical and Non-Optical Sensors," hereby incorporated by reference.

The navigation computer 26 includes a navigation processor 52. It should be understood that the navigation processor 52 could include one or more processors to control operation of the navigation computer 26. The processors can be any type of microprocessor or multi-processor system. The term processor is not intended to limit the scope any embodiment to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34. In one version, the navigation processor 52 uses well known triangulation methods for determining position data.

Prior to the start of the surgical procedure, additional data are loaded into the navigation processor 52. Based on the position and orientation of the trackers 44, 46, 48 and the previously loaded data, navigation processor 52 determines the position of the working end of the surgical tool 22 (e.g., the centroid of a surgical bur) and the orientation of the surgical tool 22 relative to the tissue against which the working end is to be applied. In some embodiments, the navigation processor 52 forwards these data to a manipulator controller 54. The manipulator controller 54 can then use the data to control the manipulator 56 as described in U.S. Pat. No. 9,119,655, entitled, "Surgical Manipulator Capable of Controlling a Surgical Instrument in Multiple Modes," the disclosure of which is hereby incorporated by reference.

In one embodiment, the manipulator 56 is controlled to stay within a preoperatively defined virtual boundary set by the surgeon (not shown), which defines the material of the femur F and tibia T to be removed by the surgical tool 22. More specifically, each of the femur F and tibia T has a target volume of material that is to be removed by the working end of the surgical tool 22. The target volumes are defined by one or more virtual cutting boundaries. The virtual cutting boundaries define the surfaces of the bone that should remain after the procedure. The navigation system 20 tracks and controls the surgical tool 22 to ensure that the working end, e.g., the surgical bur, only removes the target volume of material and does not extend beyond the virtual cutting boundary, as disclosed in U.S. Pat. No. 9,119,655, entitled, "Surgical Manipulator Capable of Controlling a Surgical Instrument in Multiple Modes," the disclosure of which is hereby incorporated by reference.

The virtual cutting boundary may be defined within a virtual model of the femur F and tibia T and be represented as a mesh surface, constructive solid geometry (CSG), voxels, or using other boundary representation techniques. The surgical tool 22 cuts away material from the femur F and tibia T to receive an implant. The surgical implants may include unicompartmental, bicompartmental, or total knee implants as shown in U.S. patent application Ser. No. 13/530,927, entitled, "Prosthetic Implant and Method of Implantation," the disclosure of which is hereby incorporated by reference.

The navigation processor 52 also generates image signals that indicate the relative position of the working end to the tissue. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

Figure 3:
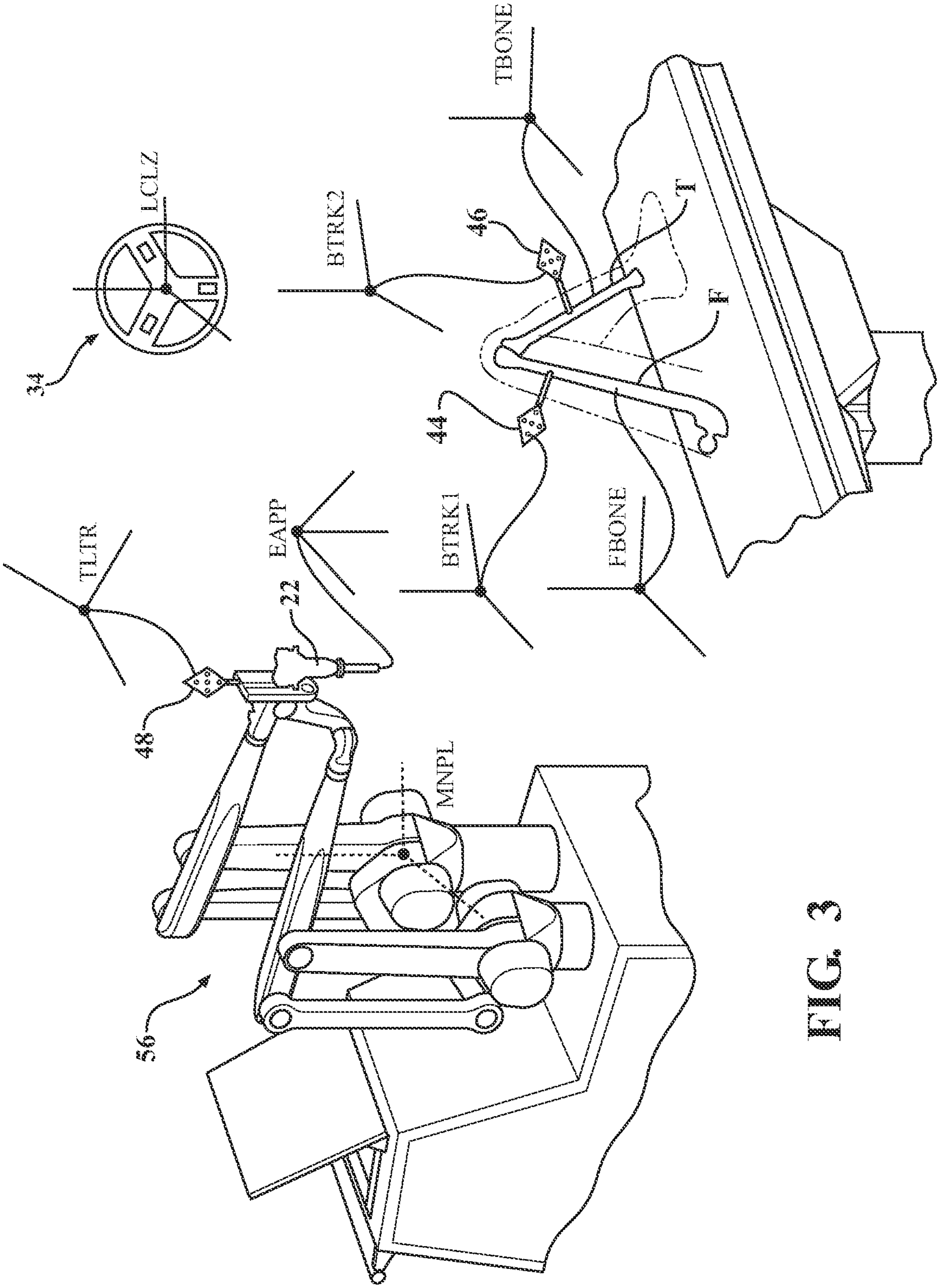
FIG. 3 is schematic view of coordinate systems used in the material removal system.

Referring to FIG. 3, tracking of objects is generally conducted with reference to a localizer coordinate system LCLZ. The localizer coordinate system has an origin and an orientation (a set of x, y, and z axes). During the procedure one goal is to keep the localizer coordinate system LCLZ in a known position. An accelerometer (not shown) mounted to the localizer 34 may be used to track sudden or unexpected movement of the localizer coordinate system LCLZ, as may occur when the localizer 34 is inadvertently bumped by surgical personnel.

Each tracker 44, 46, 48 and object being tracked also has its own coordinate system separate from the localizer coordinate system LCLZ. Components of the navigation system 20 that have their own coordinate systems are the bone trackers 44, 46 and the tool tracker 48. These coordinate systems are represented as, respectively, bone tracker coordinate systems BTRK1, BTRK2, and tool tracker coordinate system TLTR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIG. 1), such as disclosed in U.S. Pat. No. 7,725,162 to Malackowski, et al., hereby incorporated by reference, having its own tracker PT (see FIG. 1), may be used to register the femur coordinate system FBONE and tibia coordinate system TBONE to the bone tracker coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 44, 46. These pose-describing data are stored in memory integral with both manipulator controller 54 and navigation processor 52.

The working end of the surgical tool 22 (also referred to as energy applicator distal end) has its own coordinate system EAPP. The origin of the coordinate system EAPP may represent a centroid of a surgical cutting bur, for example. The pose of coordinate system EAPP is fixed to the pose of tool tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

Referring to FIG. 2, a localization engine 100 is a software module that can be considered part of the navigation system 20. Components of the localization engine 100 run on navigation processor 52. In some embodiments, the localization engine 100 may run on the manipulator controller 54.

Localization engine 100 receives as inputs the optically-based signals from the camera controller 42 and, in some embodiments, the non-optically based signals from the tracker controller. Based on these signals, localization engine 100 determines the pose of the bone tracker coordinate systems BTRK1 and BTRK2 in the localizer coordinate system LCLZ. Based on the same signals received for the tool tracker 48, the localization engine 100 determines the pose of the tool tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the bone trackers 44, 46. Coordinate transformer 102 also stores the data indicating the pose of the working end of the surgical tool 22 relative to the tool tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, PHONE and TBONE to the localizer coordinate system LCLZ.

As a result, coordinate transformer 102 generates data indicating the position and orientation of the working end of the surgical tool 22 relative to the tissue (e.g., bone) against which the working end is applied Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical tool 22.

In the embodiment shown in FIG. 1, the surgical tool 22 forms part of an end effector of the manipulator 56. The manipulator 56 has a base 57, a plurality of links 58 extending from the base 57, and a plurality of active joints (not numbered) for moving the surgical tool 22 with respect to the base 57. The manipulator 56 has the ability to operate in a manual mode or a semi-autonomous mode in which the surgical tool 22 is autonomously moved along a predefined tool path, as described in U.S. Pat. No. 9,119,655, entitled, "Surgical Manipulator Capable of Controlling a Surgical Instrument in Multiple Modes," the disclosure of which is hereby incorporated by reference.

The manipulator controller 54 can use the position and orientation data of the surgical tool 22 and the patient's anatomy to control the manipulator 56 as described in U.S. Pat. No. 9,119,655, entitled, "Surgical Manipulator Capable of Controlling a Surgical Instrument in Multiple Modes," the disclosure of which is hereby incorporated by reference.

The manipulator controller 54 may have a central processing unit (CPU) and/or other manipulator processors, memory (not shown), and storage (not shown). The manipulator controller 54, also referred to as a manipulator computer, is loaded with software as described below. The manipulator processors could include one or more processors to control operation of the manipulator 56. The processors can be any type of microprocessor or multi-processor system. The term processor is not intended to limit any embodiment to a single processor.

Figure 4:
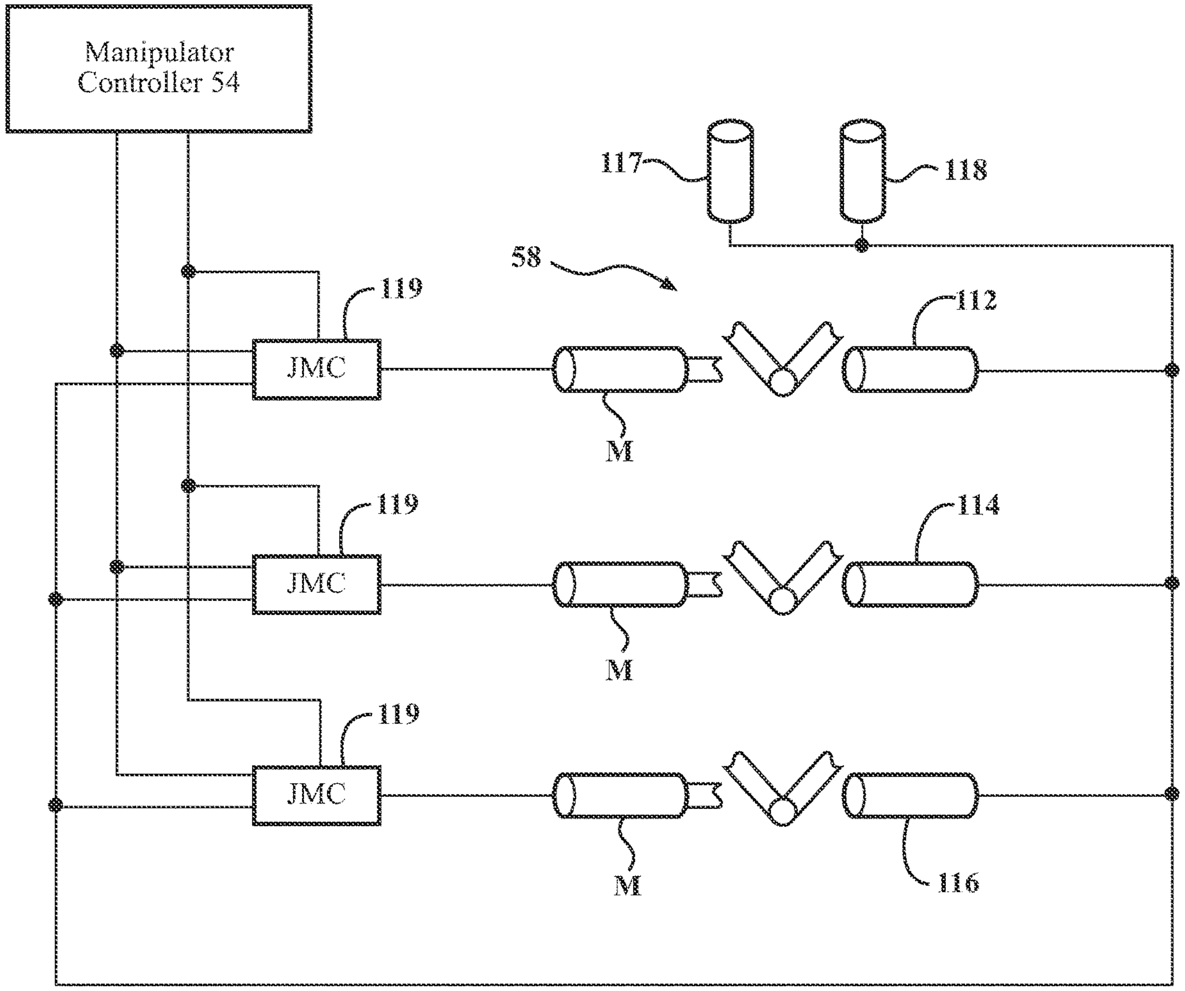
FIG. 4 is a schematic view of joint motor controllers and sensors.

Referring to FIG. 4, a plurality of position sensors 112, 114, 116 are associated with the plurality of link 58 of the manipulator 56. In one embodiment, the position sensors 112, 114, 116 are encoders. The position sensors 112, 114, 116 may be any suitable type of encoder, such as rotary encoders. Each position sensor 112, 114, 116 is associated with an actuator, such as motor M. Each position sensor 112, 114, 116 is a sensor that monitors the angular position of one of three motor driven components of the manipulator 56 with which the position sensor is associated. Manipulator 56 includes two additional position sensors, 117 and 118. Position sensors 117 and 118 are associated with additional driven links. In some embodiments, the manipulator 56 includes two arm structures with six position sensors at six active joints. One such embodiment is described in U.S. Pat. No. 9,119,655, entitled, “Surgical Manipulator Capable of Controlling a Surgical Instrument in Multiple Modes,” the disclosure of which is hereby incorporated by reference.

Manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers 119 that control the active joints of the manipulator 56 to move the plurality of links 58 and thereby move the surgical tool 22 from the current location to the desired location.

In order to determine the current location of the surgical tool 22, data from the position sensors 112, 114, 116, 117 and 118 is used to determine measured joint angles. The measured joint angles of the active joints are forwarded to a forward kinematics module, as known in the art. Also applied to the forward kinematics module are the signals from the position sensors 117 and 118. These signals are the measured joint angles for passive joints integral with these encoders. Based on the measured joint angles and preloaded data, the forward kinematics module determines the pose of the surgical tool 22 in a manipulator coordinate system MNPL. The preloaded data are data that define the geometry of the plurality of links 58 and joints. With this information, the manipulator controller 54 and/or navigation processor 52 can transform coordinates from the localizer coordinate system LCLZ into the manipulator coordinate system MNPL, or vice versa.

In one embodiment, the manipulator controller 54 and joint motor controllers 119 collectively form a position controller that operates to move the surgical tool 22 to desired positions and/or orientations. The position controller operates in a position control loop. The position control loop may include multiple position control loops in parallel or series for each active joint. The position control loop processes position and orientation information to indicate and direct the pose of the surgical tool 22.

During operation of the manipulator 56, line-of-sight between the trackers 44, 46, 48 and the localizer 34 should be maintained to ensure accurate movement of the surgical tool 22 to the desired positions and/or orientations. Periods of time in which the line-of-sight is blocked or obstructed may require the material removal system 10 to display an error message and cease operation of the manipulator 56 until the line-of-sight returns or the navigation system 20 is reset. This can cause delays in surgical procedures. This could significantly increase the surgical procedure time, particularly if difficulty arises in restoring the line-of-sight.

The navigation computer 26 determines that there is an error if any one of the optical sensors 40 fails to receive a signal from an LED 50, even though other optical sensors 40 may still receive the signal. In other embodiments, the navigation computer 26 determines that there is an error if none of the optical sensors 40 receive the signal. In either case, when the navigation system 20 determines that there is an error based on the failure of one or more optical sensors 40 to receive signals from one or more LEDs 50, an error signal is generated by the navigation computer 26. An error message then appears on displays 28, 29. The navigation computer 26 also transmits an error signal to the tracker controller.

In some embodiments, the tracker 44 may include four or more tracking LEDs 50 so that if the tracking signal from one of the LEDs 50 is obstructed, position and orientation data can still be obtained using the remaining LEDs 50. In this instance, before any error signals are generated, the navigation computer 26 will first run through a complete tracking cycle. The complete tracking cycle includes sequentially activating all the LEDs 50 on the tracker 44 to determine if the optical sensors 40 receive tracking signals from at least three of the LEDs 50 in the tracking cycle. The error signal is then generated, and the error message displayed, if an optical sensor 40 (or all optical sensors 40 in some embodiments) did not receive tracking signals from at least three LEDs 50 in the tracking cycle. In some of the embodiments described further below, the navigation system 20 reduces the potential for line-of-sight obstructions in order to avoid such error messages.

Line-of-sight obstructions block light signals being sent from the LEDs 50 of the trackers 44, 46, 48 to the optical sensors 40 of the localizer 34. The navigation system 20 reduces these line-of-sight obstructions intraoperatively, i.e., during the surgical procedure, by tracking objects that may cause such line-of-sight obstructions and generating feedback to the user should any of the objects pose a risk of blocking or obstructing the line-of-sight between one of the tracking devices 44, 46, 48 and the localizer 34.

Objects that can cause line-of-sight obstructions include any physical objects that may be within the field-of-view of the localizer 34 during the surgical procedure. Examples of such physical objects include the structures associated with each of the trackers 44, 46, 48, or portions thereof. Other physical objects may include the surgical tool 22, retractors at the surgical site, a limb holder, other tools, surgical personnel, or portions of any of these, that may be within the field-of-view of the localizer 34. If unchecked, these physical objects could move in a way that causes a line-of-sight obstruction. The navigation system 20 tracks the positions and orientations of each of these physical objects and generates feedback to the user before a line-of-sight obstruction arises to at least reduce, and ideally prevent, line-of-sight obstructions.

Each of the physical objects that can cause line-of-sight obstructions are modeled in virtual space for purposes of tracking these physical objects. These models are referred to as virtual objects. Virtual objects are maps in the localizer coordinate system LCLZ of each of the physical objects being tracked in the field-of-view of the localizer 34 such as the trackers 44, 46, 48, the surgical tool 22, the retractors, the limb holder, other tools, or surgical personnel. The virtual objects could be represented by polygonal surfaces, splines, or algebraic surfaces (including parametric surfaces). In one more specific version, these surfaces are presented as triangular meshes. The corners of each polygon are defined by points in the localizer coordinate system LCLZ. An individual area section that defines a portion of each virtual object boundary or mesh is referred to as a tile. The virtual objects can also be represented by 3-D volumes using voxel-based models or other modeling techniques.

Figure 5:
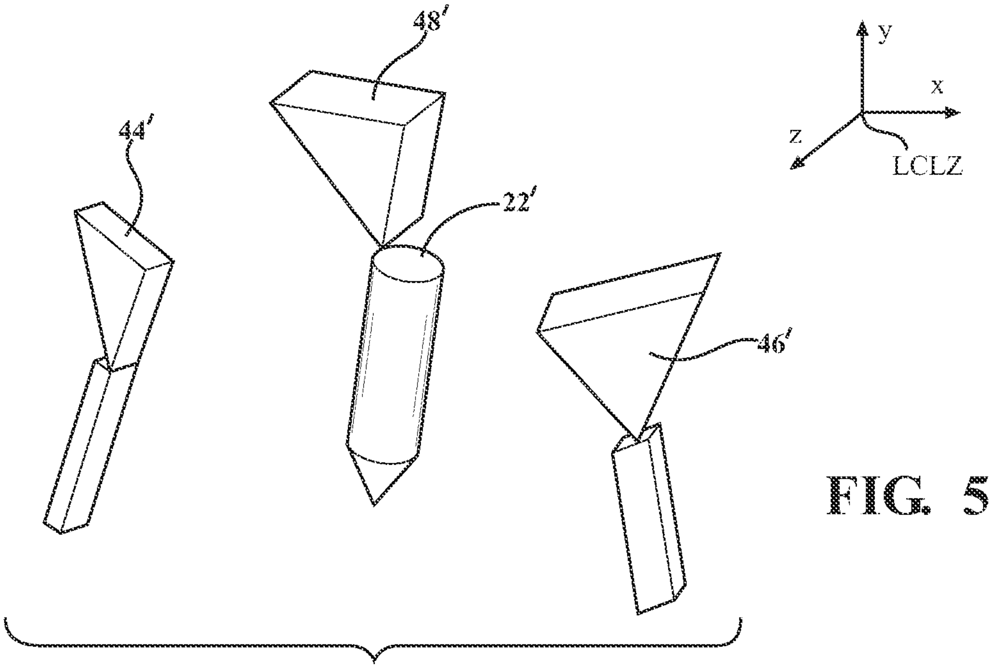
FIG. 5 illustrates virtual objects in a localizer coordinate system.

Referring to FIG. 5, for purposes of illustration, virtual objects 44', 46', 48', 22' associated with the physical structures of the trackers 44, 46, 48 and the surgical tool 22 are shown in the localizer coordinate system LCLZ. Note that the virtual objects 44', 46', 48', 22' are modeled as simple shapes for purposes of computational efficiency. Additionally, the tool tracker and tool virtual objects 48' and 22' associated with the tool tracker 48 and the surgical tool 22 are fixed relative to one another and could alternatively be represented as a single virtual object.

The tool tracker and tool virtual objects 48' and 22' can be tracked by virtue of tracking the tool tracker 48. In particular, the geometric models of the tool tracker and tool virtual objects 48' and 22' are stored in memory and their relationships to the LEDs 50 on the tool tracker 48 are known. The bone tracker virtual objects 44' and 46' can be tracked by virtue of tracking the bone trackers 44, 46. In particular, the geometric models of the bone tracker virtual objects 44' and 46' are stored in memory and their relationships to the LEDs 50 on the bone trackers 44, 46 are known. Other tracking devices (not shown) may be attached to other physical objects, such as the retractors, the limb holder, other tools, or surgical personnel present in the field-of-view of the localizer 34 in order to track these other physical objects.

Figure 6:
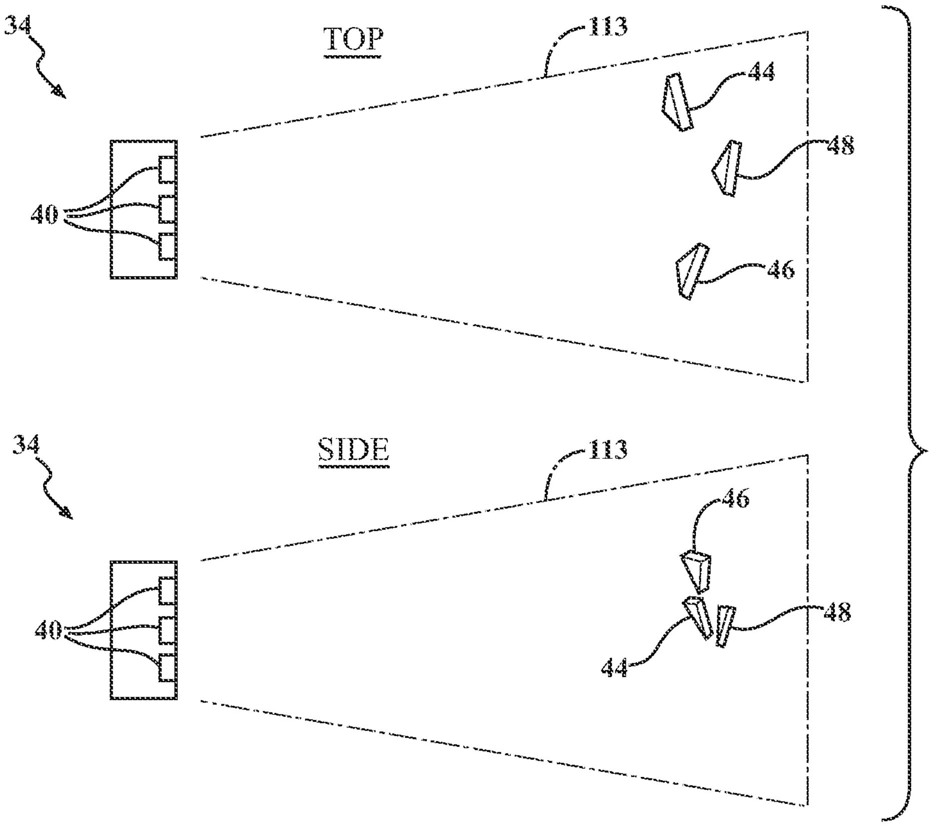
FIG. 6 illustrates top and side views of a field-of-view of a localizer and trackers located in the field-of-view.

Before the surgical procedure begins, each of the trackers 44, 46, 48 are placed into the field-of-view of the localizer 34. The displays 28, 29 graphically depict the field-of-view of the localizer 34 from a top and side perspective, as shown in FIG. 6 in order to visually confirm that the trackers 44, 46, 48 are placed into the field-of-view of the localizer 34. The field-of-view is defined by the spatial relationship of the optical sensors 40 and the range of the optical sensors 40 for receiving light from the LEDs 50 of the trackers 44, 46, 48. The navigation system 20 then verifies that each of the trackers 44, 46, 48 is visible in the field-of-view. Once verified, the surgical procedure can begin.

Figure 7:
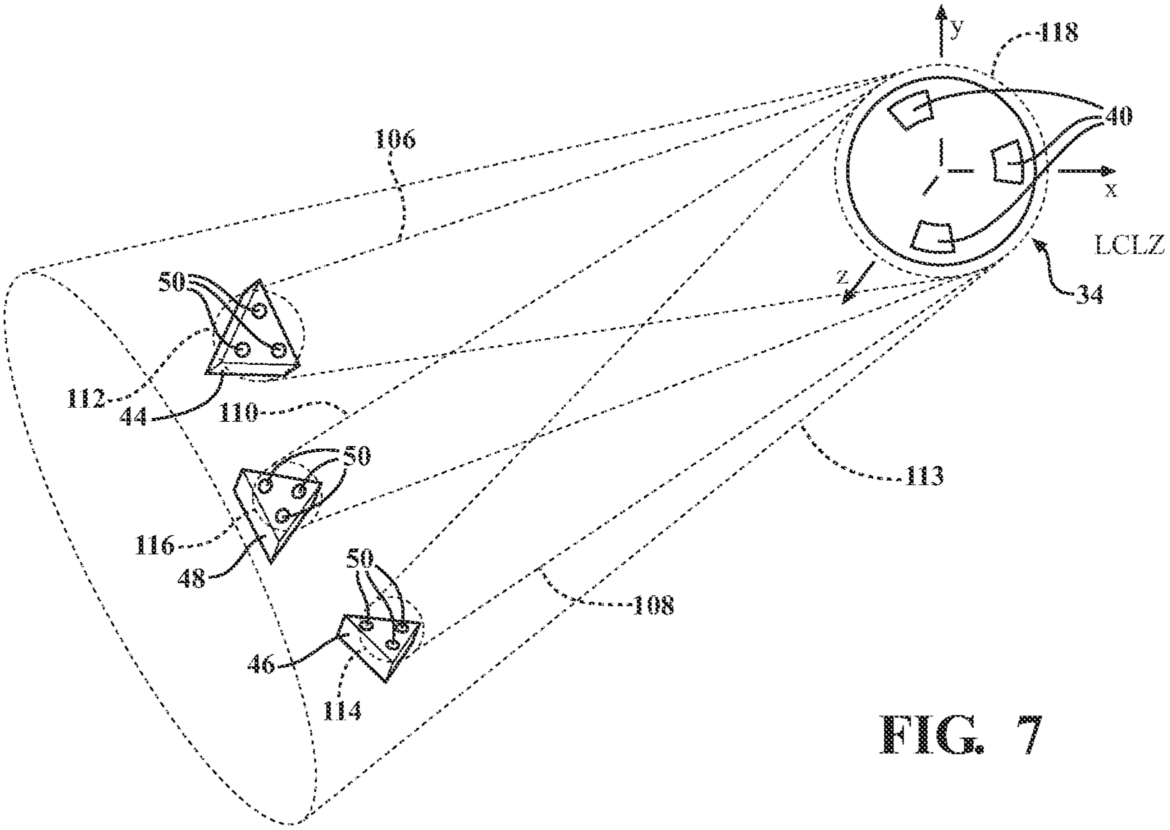
FIG. 7 illustrates virtual line-of-sight boundaries between the trackers and the localizer.

Referring to FIG. 7, a virtual boundary generator 104 (see FIG. 2) generates a virtual line-of-sight boundary 106, 108, 110 based on the line-of-sight relationship between each of the tracking devices 44, 46, 48 and the localizer 34. The virtual line-of-sight boundary 106, 108, 110 delineates space in which the physical objects should be restricted from entering so that light from the LEDs 50 of each tracking device 44, 46, 48 is able to be transmitted, without obstruction or blockage, to the optical sensors 40 of the localizer 34.

In some embodiments the virtual line-of-sight boundaries 106, 108, 110 are cylindrical, spherical, or frustoconical in shape, as shown in FIG. 7. Other shapes are also possible. In other embodiments, the virtual line-of-sight boundaries are represented as lines (e.g., lines from each of the LEDs to each of the optical sensors 40). The virtual line-of-sight boundaries 106, 108, 110 shown in FIG. 7 extend from a first end 112, 114, 116 defined about the LEDs 50 on each of the tracking devices 44, 46, 48 to a second end 118 defined about the optical sensors 40 of the localizer 34. The virtual line-of-sight boundaries 106, 108, 110 may be oversized such that the physical objects may penetrate slightly into the virtual line-of-sight boundaries in order to detect collisions, as explained further below, without causing a line-of-sight obstruction.

The virtual boundary generator 104 updates the virtual line-of-sight boundaries 106, 108, 110 to account for relative movement between the tracking devices 44, 46, 48 and the localizer 34 during the surgical procedure. Updating may occur each time the navigation system 20 receives a complete set of signals from the LEDs 50 for each of the tracking devices 44, 46, 48 (e.g., at least three signals for each tracking device). Updating may occur each time a new commanded position is determined for the surgical tool 22. In embodiments in which the surgical tool 22 is controlled by the manipulator 56, the time frame for determining each new commanded position may be every 0.1 to 2 milliseconds.

The virtual boundary generator 104 is a software module that runs on the navigation processor 52 or the manipulator controller 54, or both. The virtual boundary generator 104 generates a map that defines the virtual line-of-sight boundaries 106, 108, 110. A first input into the virtual boundary generator 104 includes the position and orientation of each of the LEDs 50 for each of the tracking devices 44, 46, 48 in the localizer coordinate system LCLZ. From this LED pose data, the position and orientation of the first end 112, 114, 116 can be defined. A second input into the virtual boundary generator 104 includes the position and orientation of each of the optical sensors 40 of the localizer 34 in the localizer coordinate system LCLZ. From this optical sensor pose data, the position and orientation of the second end 118 about the optical sensors 40 can be defined. Based on the above data and through instructions, the virtual boundary generator 104 generates the map that defines the virtual line-of-sight boundaries 106, 108, 110 in the localizer coordinate system LCLZ.

In some embodiments, the virtual boundary generator 104 generates the virtual line-of-sight boundaries as polygonal surfaces, splines, or algebraic surfaces (including parametric surfaces). In one more specific version, these surfaces are presented as triangular meshes. The corners of each polygon are defined by points in the localizer coordinate system LCLZ. An individual area section that defines a portion of each virtual line-of-sight boundary or mesh is referred to as a tile. The virtual line-of-sight boundaries can also be represented as 3-D volumes using voxel-based models or other modeling techniques.

A collision detector 120 (see FIG. 2) evaluates movement of the virtual objects 44', 46', 48', 22' relative to the virtual line-of-sight boundaries 106, 108, 110 to detect collisions between the virtual objects 44', 46', 48', 22' and the virtual line-of-sight boundaries 106, 108, 110 (which are effectively virtual objects as well). More specifically, the collision detector 120 detects collisions between the geometric models representing the virtual objects 44', 46', 48', 22' and the geometric models representing the virtual line-of-sight boundaries 106, 108, 110. Collision detection includes detecting actual virtual collisions or predicting virtual collisions before they occur.

The purpose of the tracking performed by the collision detector 120 is to prevent any physical objects from obstructing the line-of-sight between the LEDs 50 of the tracking devices 44, 46, 48 and the optical sensors 40 of the localizer 34. A first input into the collision detector 120 is a map of each of the virtual objects 44', 46', 48', 22' being tracked in the field-of-view of the localizer 34. A second input into the collision detector 120 is the map of each of the virtual line-of-sight boundaries 106, 108, 110.

The collision detector 120 is a software module that runs on the navigation processor 52 or the manipulator controller 54, or both. The collision detector 120 may use any algorithm for detecting collisions between the virtual objects 44', 46', 48', 22' and the virtual line-of-sight boundaries 106, 108, 110. For example, suitable techniques for finding the intersection of two parametric surfaces include subdivision methods, lattice methods, tracing methods, and analytic methods. For voxel-based virtual objects, collision detection can be carried out by detecting when any two voxels overlap in the localizer coordinate system LCLZ, as described in U.S. Pat. No. 5,548,694, hereby incorporated by reference.

A feedback generator 122 (see FIG. 2) is in communication with the collision detector 120 to respond to the detection of a collision between any of the virtual objects 44', 46', 48', 22' and any of the virtual line-of-sight boundaries 106, 108, 110. The feedback generator 122 is a software module that runs on the navigation processor 52 or the manipulator controller 54, or both. The feedback generator 122 responds to the detection of a collision by providing the user with one or more forms of feedback, including one or more of audible, visual, vibration, or haptic feedback.

In one embodiment, the feedback generator 122 causes activation of a feedback device in the form of an annunciator 124 in communication with the navigation processor 52 to produce an audible alert to the user in response to a collision.

Figure 8:
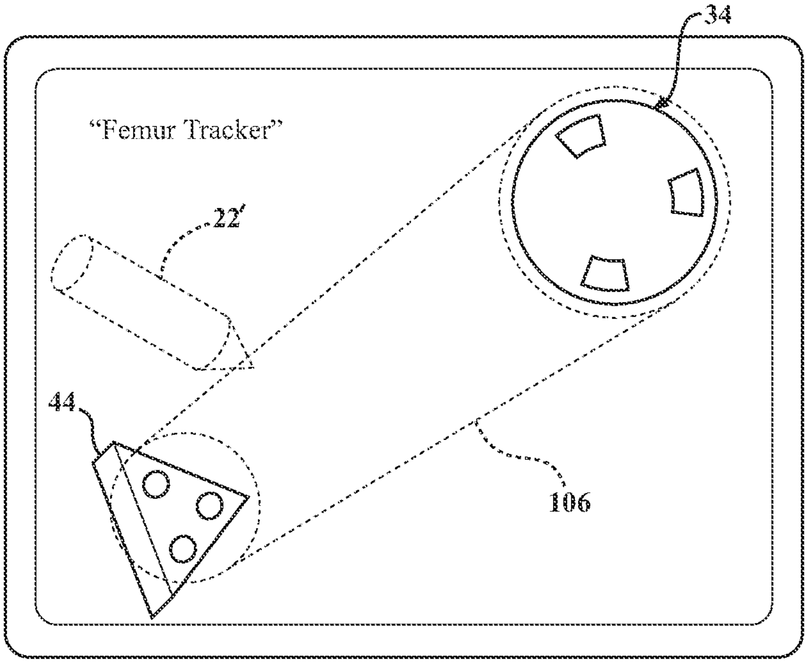
FIG. 8 is a screen shot of a display illustrating a collision between a virtual object and a virtual line-of-sight boundary.

Referring to FIG. 8, the feedback generator 122 may also cause the displays 28, 29 to display an image representing the collision so that the user can determine how to avoid the collision (in the case that the collision has been predicted) or reverse the collision (in the case that the collision has already occurred). The collision may be represented by showing the virtual line-of-sight boundary 106, 108 or 110 being affected, along with a graphic representation of where the physical object involved has collided with or is about to collide with the virtual line-of-sight boundary 106, 108, 110. A text description of the particular tracker 44, 46, or 48 involved, i.e., the tracker that is about to be obstructed, such as "femur tracker," may also be displayed on the displays 28, 29.

In some embodiments, every physical object in the field-of-view of the localizer 34 that is tracked using virtual objects could be represented on the displays 28, 29. In this case, the collision may be illustrated using color coding. For instance, the color red could be shown surrounding the portion of the physical object (associated by virtue of its virtual object) colliding with the virtual line-of-sight boundary 106, 108, or 110. The tracker 44, 46, or 48 being affected could also be color coded (possibly the same or a different color) so that visually the user immediately sees which physical object is going to obstruct which tracker line-of-sight, and intuitively the user can avoid the obstruction. In addition, arrows could be graphically depicted on the display to show the direction in which the physical object should be moved to avoid the collision or reverse the collision. These arrows could be generated based on the direction of a feedback force determined by the collision detector 120, as described further below.

Figure 9:
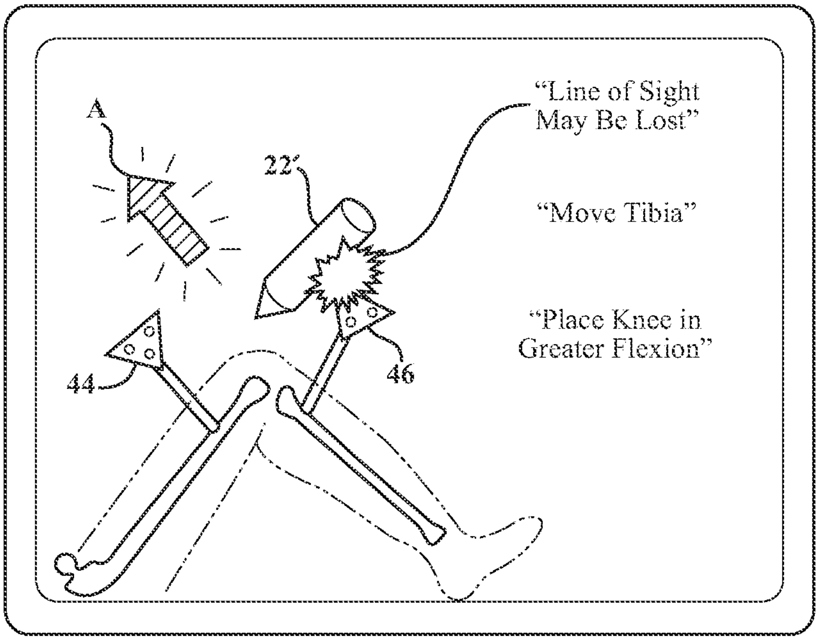
FIG. 9 is a screen shot of a display illustrating instructions to the user to avoid a line-of-sight obstruction.

Referring to FIG. 9, the feedback generator 122, in response to detecting the collision, may also cause the displays 28, 29 to display a message to the user including instructions to reposition particular anatomy of the patient. The particular anatomy may include the anatomy to which the bone tracker 44, 46 about to be obstructed is attached. For instance, if the tool virtual object 22' representing the surgical tool 22 was found to have collided with the virtual line-of-sight boundary 108 associated with the bone tracker 46 on the tibia T, the navigation processor 52 may cause the displays 28, 29 to display a message to the user to "move the tibia." The particular message may be stored in a look-up table of messages that are associated with particular scenarios of possible collisions. In this example, this message is located in the look-up table with the scenario in which the tool virtual object 22' has collided with the virtual line-of-sight boundary 108. More detailed instructions are also possible based on an avoidance or repulsion vector that defines the direction to be taken to avoid or reverse the collision. The instructions may be to "move the tibia" with an arrow A further displayed or flashing on the displays 28, 29, as shown in FIG. 9, wherein the arrow A is in the direction of the avoidance or repulsion vector.

The feedback generator 122 may also cause the displays 28, 29 to display a message to the user including instructions to reposition the localizer 34 in response to detecting the collision. For instance, if the tool virtual object 22' representing the surgical tool 22 was found to have collided with the virtual line-of-sight boundary 108 associated with the bone tracker 46 on the tibia T, the navigation processor 52 may cause the displays 28, 29 to display a message to the user to "move the camera unit." The particular message may be stored in a look-up table of messages that are associated with particular scenarios of possible collisions. In this example, this message is located in the look-up table with the scenario in which the tool virtual object 22' has collided with the virtual line-of-sight boundary 108.

The feedback generator 122 may also cause the displays 28, 29 to display a message to the user including instructions to reposition the manipulator 56 in response to detecting the collision. For instance, if the tool virtual object 22' representing the surgical tool 22 was found to have collided with the virtual line-of-sight boundary 108 associated with the bone tracker 46 on the tibia T, the navigation processor 52 may cause the displays 28, 29 to display a message to the user to "move the manipulator." The particular message may be stored in a look-up table of messages that are associated with particular scenarios of possible collisions. In this example, this message is located in the look-up table with the scenario in which the tool virtual object 22' has collided with the virtual line-of-sight boundary 108. One reason this feedback may be used is in situations in which the surgical tool 22 or tibia T cannot otherwise be manipulated to avoid the collision. Additionally, the manipulator 56 has a limited range of motion and if the manipulator 56 is within a predefined threshold of that limited range, this message may be needed to regain additional range of motion during the surgical procedure to avoid collisions.

In addition, the feedback generator 122 may cause the user to experience vibration feedback in the form of vibrations to the physical object associated with the virtual object 44', 46', 48', 22' that is colliding with or about to collide with a virtual line-of-sight boundary 106, 108, 110. For instance, when the user is positioning the surgical tool 22 in a manual mode in which the user is grasping a handle of the surgical tool 22, a vibration device 126, such as an eccentric motor, may be actuated if the tool virtual object 22' is colliding with or about to collide with a virtual line-of-sight boundary 106, 108, 110. The vibration device 126 is mounted to the surgical tool 22 such that vibrations from the vibration device 126 can be transmitted to the handle. The vibration feedback indicates to the user that the intended position may cause a line-of-sight obstruction thereby allowing the user to cease further motion and prevent the line-of-sight obstruction. The user can then determine an alternate course that will avoid a line-of-sight obstruction.

In one embodiment, the feedback generator 122 provides haptic feedback to the user by responding to a collision with a feedback force that avoids or repulses the collision. The feedback force is determined by the collision detector 120. The feedback force may have force and/or torque components including up to three components of force along x, y, and z axes, and three components of torque about these axes.

In one example, the feedback generator 122 provides the haptic feedback to the user through the surgical tool 22 when the manipulator 56 is operated in the manual mode. This prevents the manipulator 56 from positioning the tool virtual object 22' associated with the surgical tool 22 into the virtual line-of-sight boundaries 106, 108 associated with the bone trackers 44, 46 thereby avoiding any line-of-sight obstruction. In one embodiment, the collision detector 120 detects the collision by predicting whether a virtual collision will occur if the manipulator 56 moves the surgical tool 22 to a commanded pose, but before the manipulator controller 54 actually moves the surgical tool 22 to the commanded pose. If a virtual collision is predicted, then the manipulator 56 is controlled to move the surgical tool 22 to an altered commanded pose to avoid the collision.

In some embodiments, the manipulator 56 is a passive manipulator. In this case, the haptic feedback provides feedback to the user after a virtual collision occurs to prevent any further penetration of the virtual object 44', 46', 48', 22' into the affected virtual line-of-sight boundary 106, 108, 110 or to reverse the collision. Thus, the collision detection may be responsive to an actual virtual collision or a predicted virtual collision. The feedback generator 122 thus ensures that the manual mode positioning of the surgical tool 22 is controlled so that the tool virtual object 22' stays outside of, or only penetrates so far into, the virtual line-of-sight boundaries 106, 108 to prevent the surgical tool 22 from causing line-of-sight obstructions between the bone trackers 44, 46 and the localizer 34.

When the virtual line-of-sight boundaries 106, 108 are represented by a polygonal surface such as a mesh, the collision detector 120 identifies any boundary-defining tiles that the tool virtual object 22' could cross during a time frame. This step is often described as a broad phase search. This step is performed by identifying the set or sets of tiles that are within a defined distance (d) of the tool virtual object 22'. This defined distance (d) is a function of: the dimensions of the tool virtual object 22'; the velocity of the tool virtual object 22' relative to the tiles (the velocity of advancement during the past frame is acceptable); the time period of the frame; a scalar defining a characteristic size of the boundary defining sections; and a rounding factor.

Figure 10:
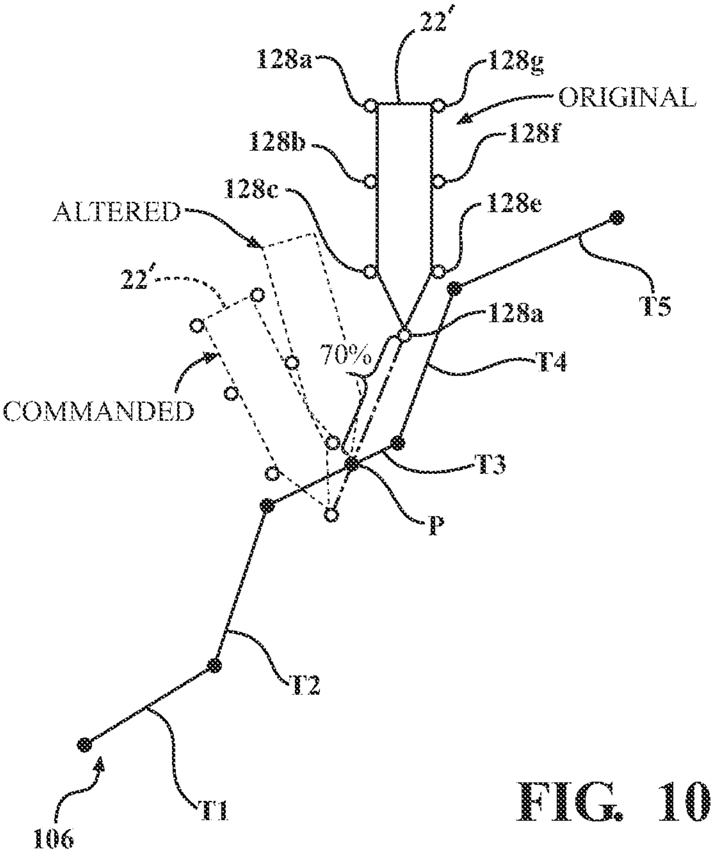
FIG. 10 illustrates a virtual object crossing a virtual line-of-sight boundary and the associated feedback force generated to avoid or repulse the collision.

As a result of the execution of the broad phase search, the collision detector 120 may determine that, in the frame for which this analysis is being performed, all of the tiles are outside of the defined distance (d). This means that, by the end of the frame for which this analysis is being performed, the tool virtual object 22' will not have advanced to a location beyond either of the virtual line-of-sight boundaries 106, 108. This is illustrated by FIG. 10 where the tool virtual object 22', is spaced well away from the virtual line-of-sight boundary 106. It should be appreciated that this analysis may be conducted for a set of points defining the tool virtual object 22', such as points 128*a*-128*g* defining an outer surface of the tool virtual object 22', with each point being analyzed to detect whether that particular point will cross the virtual line-of-sight boundary 106.

Since the continued advancement of the surgical tool 22 will not cause any line-of-sight obstructions, the collision detector 120 does not modify either the commanded pose or the commanded velocity of the surgical tool 22 originally commanded by the manipulator controller 54. The collision detector 120 thus outputs a final commanded pose and a final commanded velocity for the surgical tool 22 that is the same as that originally determined by the manipulator controller 54.

The collision detector 120 may alternatively identify a broad set of boundary-defining tiles that are within the defined distance (d) of the tool virtual object 22' or the points 128*a*-128*g*. The collision detector 120 then identifies a narrow set of boundary-defining tiles that are within the broad set of tiles that the tool virtual object 22', or any of points 128*a*-128*g* on the tool virtual object 22' could cross. This step is referred to as the narrow phase search. This narrow phase search can be performed by initially defining a bounding volume. This bounding volume extends between what are considered to be initial and final poses of the tool virtual object 22'. If this is the first execution, the initial pose of the tool virtual object 22' is based on the previous commanded pose of the surgical tool 22; the final pose of the tool virtual object 22' is based on the current commanded pose of the surgical tool 22, i.e., the pose generated by the manipulator controller 54 to which the surgical tool 22 should be moved in this frame if the collision detector 120 does not detect any collisions.

In its most elemental form, the bounding volume may be lines extending from the points 128*a*-128*g* in the initial pose to the points 128*a*-128*g* in the final pose. Once the bounding volume is defined, as part of the narrow phase search, the collision detector 120 determines which, if any, of the broad set of tiles are intersected by this bounding volume. The tiles intersected by the bounding volume are the narrow set tiles.

It may be determined that none of the broad set of tiles are intersected by the bounding volume; the narrow set is an empty set. If this evaluation tests true, the collision detector 120 interprets this condition as indicating that the final pose of the tool virtual object 22' is outside the volumes defined by the virtual line-of-sight boundaries 106, 108. If the tool virtual object 22' is so located, the original commanded pose and commanded velocity are unaltered by the collision detector 120 and are output by the collision detector 120 as the final commanded pose and final commanded velocity.

Alternatively, it may be determined that the bounding volume crosses one or more tiles; the narrow set contains one or more tiles. If so, the collision detector 120 interprets this condition as indicating that the final pose of the tool virtual object 22' is penetrating a boundary. This condition is illustrated by FIG. 10. Here the initial pose of the tool virtual object 22' is represented by solid lines and the final pose is represented by phantom lines.

If the condition of intruding on a virtual line-of-sight boundary 106, 108 exists, the next step is to determine which of the narrow set of tiles the tool virtual object 22' (and by extension the surgical tool 22) would cross first. If the bounding volume comprises lines, the collision detector 120, for each tile, and for each line, determines the percentage of distance the surgical tool virtual object 22' will advance during the frame prior to crossing the tile (see note of seventy percent in FIG. 10). The tile crossed at the lowest percentage of distance is the tile understood to be crossed first.

The boundary defining tiles closest to the tool virtual object 22' may not be the tiles that the tool virtual object 22' could cross. As shown in FIG. 10, it was initially determined that tiles T1-T5 of the virtual line-of-sight boundary 106 are within the defined distance (d), the distance the tool virtual object 22' could potentially move within the time frame. The closest tile to the tool virtual object 22' is tile T4. However, the tool virtual object 22' is moving along a trajectory that is, for purposes of illustration, downward and to the left towards tile T3. Therefore, the collision detector 120 determines that tile T3 is the tile the bounding volume would intersect.

Once the collision detector 120 generally determines which boundary-defining tile the tool virtual object 22' will cross if the manipulator controller 54 moves the surgical tool 22 to the originally commanded pose, the collision detector 120 determines a time (t) and a point P. Time (t) is the time period relative to the start of the frame, when the tool virtual object 22' will cross the virtual line-of-sight boundary 106. This time (t) is determined based on the percentage of distance the tool virtual object 22' will advance during the frame prior to contacting the virtual line-of-sight boundary 106, which in this case is seventy percent of the distance, as shown in FIG. 10. This determination is made based on the assumption that, during any given frame, the velocity of the surgical tool 22, and thus the tool virtual object 22' is constant. Point P is the point in the localizer coordinate system LCLZ where the tool virtual object 22' will cross the tile. This point P is determined by calculating where the path of advancement of the tool virtual object 22' crosses the tile. Both calculations use as input variables the initial and final poses of the particular point 128*a*-128*g* that crosses a tile first and data defining the perimeter of the boundary tile.

In some embodiments, in this situation, the original commanded pose is altered by the collision detector 120 to be the position and orientation that the surgical tool 22 reaches before contacting the virtual line-of-sight boundary 106, e.g., the position and orientation reached at seventy percent of the distance/time. The user, by virtue of grasping the surgical tool 22 with an expectation of moving the surgical tool 22 the entire one hundred percent of movement would experience haptic feedback similar to encountering a physical wall when movement ceased at seventy percent, i.e., only to the altered position and orientation. Thus, the manipulator 56 to which the surgical tool 22 is attached is considered to be a haptic device that transmits haptic feedback to the user.

In another embodiment, the feedback generator 122 determines a feedback force to be applied to the surgical tool 22 (modeled as a virtual rigid body) to stop the unwanted progression of the surgical tool 22 beyond the virtual line-of-sight boundary 106. The feedback generator 122 determines the feedback force as a boundary constraining force applied to the surgical tool 22. More specifically, the feedback generator determines a scalar feedback force FBNDR that, if applied to the surgical tool 22 at time (t), would stop the advancement of the surgical tool 22 in the direction normal to and towards the virtual line-of-sight boundary 106. The feedback generator 122 may use any one of a number of different methods to determine the magnitude of force FBNDR. For instance, an impulse method may be used, as described in U.S. Pat. No. 9,119,655, entitled, "Surgical Manipulator Capable of Controlling a Surgical Instrument in Multiple Modes," the disclosure of which is hereby incorporated by reference.

The final commanded pose and commanded velocity are then calculated to account for the force FBNDR. As opposed to merely ceasing movement of the surgical tool 22 at seventy percent to prevent contacting the virtual line-of-sight boundary 106, this method only ceases the component of movement that is normal to the virtual line-of-sight boundary 106, by virtue of the impulse force. Thus, movement along the virtual line-of-sight boundary 106 may continue the entire time frame to provide a more natural haptic feedback to the user, as opposed to an abrupt stop.

Ultimately, the final commanded pose from the collision detector 120 is applied to an inverse kinematics module (not shown) of the manipulator controller 54. The inverse kinematics module is a motion control module executed by the manipulator controller 54. Based on the commanded pose and preloaded data, the inverse kinematics module determines the desired joint angle of the joints of the manipulator 56. The preloaded data are data that define the geometry of the links 58 and joints. In some versions, these data are in the form of Denavit-Hartenberg parameters.

As previously discussed, before the surgical procedure begins, each of the trackers 44, 46, 48 are placed into the field-of-view of the localizer 34. The navigation system 20, which operates to reduce line-of-sight obstructions, also operates to maintain the trackers 44, 46, 48 within the field-of-view. In particular, the navigation system 20 operates to maintain the trackers 44, 46, 48 within the field-of-view intraoperatively, i.e., during the surgical procedure, by tracking movement of the trackers 44, 46, 48 during the surgical procedure and generating feedback to the user should any of the trackers 44, 46, 48 pose a risk of moving outside of the field-of-view of the localizer 34.

The field-of-view of the localizer 34 is shown from a top and side view in FIG. 6. The virtual boundary generator 104 also generates a virtual field-of-view boundary 113 based on the field-of-view of the localizer 34. The virtual field-of-view boundary 113 delineates a volume of space in which signals from the trackers 44, 46, 48 can be received by the localizer 34 for purposes of determining the position and/or orientation of the trackers 44, 46, 48. In other words, signals from at least three LEDs 50 of each tracker 44, 46, 48 can be received by each of the optical sensors 40 of the localizer 34.

In some embodiments the virtual field-of-view boundary 113 is frustoconical in shape, as shown in FIG. 7. In other embodiments, the virtual field-of-view boundary 113 is cylindrical or spherical in shape. Other shapes are also possible. The virtual field-of-view boundary 113 shown in FIG. 7 extends divergently outward from the localizer 34 to a distal end. The virtual field-of-view boundary 113 may be oversized such that the virtual objects 44', 46', 48' representing the trackers 44, 46, 48 may penetrate slightly into the virtual field-of-view boundary 113 in order to detect collisions, as explained further below, without moving beyond the actual field-of-view of the localizer 34.

The virtual field-of-view boundary 113 is intended to remain static during the surgical procedure, but may require adjustment should the localizer 34 be moved during the surgical procedure. In this case, the virtual boundary generator 104 updates the virtual field-of-view boundary 113 to account for such movement during the surgical procedure.

The virtual boundary generator 104 generates a map that defines the virtual field-of-view boundary 113. An input into the virtual boundary generator 104 includes the position and orientation of the localizer 34 in the localizer coordinate system LCLZ, i.e., the locations/arrangement of the optical position sensors 40 in the localizer coordinate system LCLZ, which is established during manufacturing (e.g., measured by a CMM) and stored in memory in the camera unit 36 or the navigation computer 26. From this localizer pose data, the position and orientation of the virtual field-of-view boundary 113 can be established. The virtual field-of-view boundary 113 can also be established during manufacturing and stored in the memory of the camera unit 36 or the navigation computer 26. The size and shape of the virtual field-of-view boundary 113 is predetermined before the surgical procedure and is fixed in position with respect to the localizer 34. Data associated with the size and shape of the virtual field-of-view boundary 113 is stored in the memory on the camera unit 36 and/or navigation computer 26 for retrieval by the navigation processor 52. Based on the above data and through instructions, the virtual boundary generator 104 generates the map that defines the virtual field-of-view boundary 113 in the localizer coordinate system LCLZ.

In some embodiments, the virtual boundary generator 104 generates the virtual field-of-view boundary 113 as a polygonal surface, splines, or algebraic surface (including parametric surface). In one more specific version, the surface is presented as triangular meshes. The corners of each polygon are defined by points in the localizer coordinate system LCLZ. An individual area section that defines a portion of the mesh is referred to as a tile. The virtual field-of-view boundary 113 can also be represented as a 3-D volume using voxel-based models.

The collision detector 120 evaluates movement of the bone tracker and tool tracker virtual objects 44', 46', 48' relative to the virtual field-of-view boundary 113 to detect collisions between the virtual objects 44', 46', 48' and the virtual field-of-view boundary 113 (which is effectively a virtual object as well). More specifically, the collision detector 120 detects collisions between the geometric models representing the virtual objects 44', 46', 48', and the geometric model representing the virtual field-of-view boundary 113. Collision detection includes detecting actual virtual collisions or predicting virtual collisions before they occur.

The purpose of the tracking performed by the collision detector 120 is to prevent the trackers 44, 46, 48 from moving outside of the field-of-view of the localizer 34. A first input into the collision detector 120 is a map of each of the virtual objects 44', 46', 48' being tracked in the field-of-view of the localizer 34. A second input into the collision detector 120 is the map of the virtual field-of-view boundary 113.

The collision detector 120 may use any algorithm for detecting collisions between the virtual objects 44', 46', 48' and the virtual field-of-view boundary 113. For example, suitable techniques for finding the intersection of two parametric surfaces include subdivision methods, lattice methods, tracing methods, and analytic methods. For voxel-based virtual objects, collision detection can be carried out by detecting when any two voxels overlap in the localizer coordinate system LCLZ, as described in U.S. Pat. No. 5,548,694, hereby incorporated by reference.

The feedback generator 122 responds to the detection of a collision between any of the virtual objects 44', 46', 48' and the virtual field-of-view boundary 113. The feedback generator 122 responds to the detection of a collision by providing the user with one or more forms of feedback, including one or more of audible, visual, vibration, or haptic feedback.

In one embodiment, the feedback generator 122 causes activation of the annunciator 124 to produce an audible alert to the user in response to a collision.

The feedback generator 122 may also cause the displays 28, 29 to display an image representing the collision so that the user can determine how to avoid the collision (in the case that the collision has been predicted) or reverse the collision (in the case that the collision has already occurred). The collision may be represented by showing a graphic representation of where the tracker involved has collided with or is about to collide with the virtual field-of-view boundary 113. A text description of the particular tracker 44, 46, or 48 involved, such as "femur tracker," may also be displayed on the displays 28, 29.

In some embodiments, every tracker 44, 46, 48 in the field-of-view of the localizer 34 that is tracked using virtual objects could be represented on the displays 28, 29. In this case, the collision may be illustrated using color coding. For instance, the tracker 44, 46, or 48 being affected could be color coded so that visually the user immediately sees which tracker is going to move outside the field-of-view, and intuitively the user can avoid such movement. In addition, arrows could be graphically depicted on the display to show the direction in which the tracker should be moved to stay within the field-of-view. These arrows could be generated based on the direction of a feedback force determined by the collision detector 120 in the manner previously described.

Figure 11:
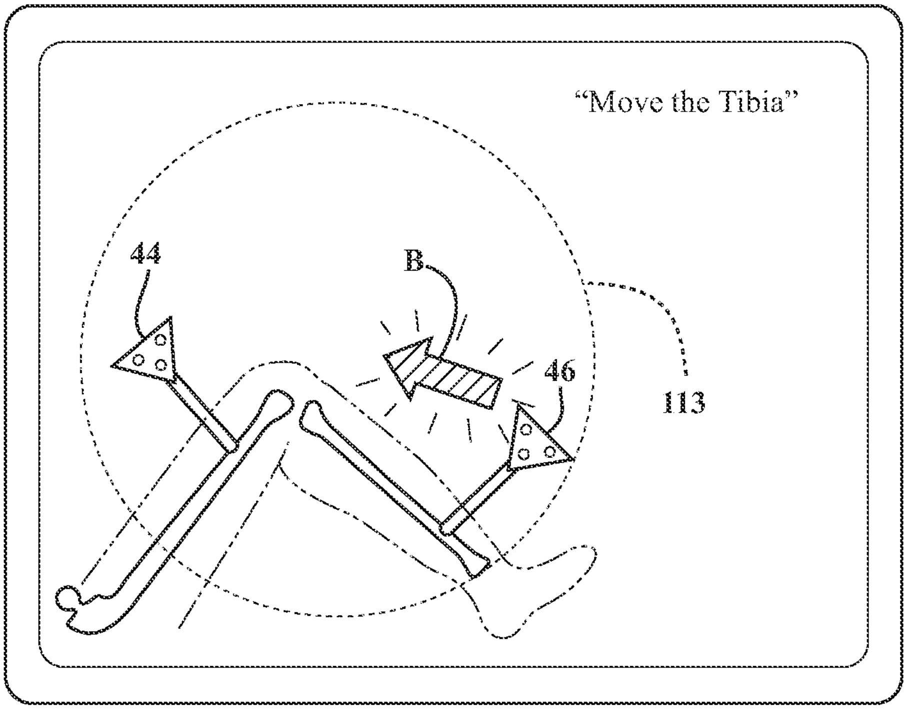
FIG. 11 is a screen shot of a display illustrating instructions to the user to avoid a tracker moving outside the field-of-view.

Referring to FIG. 11, the feedback generator 122, in response to detecting the collision, may also cause the displays 28, 29 to display a message to the user including instructions to reposition particular anatomy of the patient. The particular anatomy may include the anatomy to which the bone tracker 44, 46 about to move outside the field-of-view is attached. For instance, if the bone tracker 46 on the tibia T is about to move outside the field-of-view of the localizer 34, the navigation processor 52 may cause the displays 28, 29 to display a message to the user to "move the tibia." The particular message may be stored in a look-up table of messages that are associated with particular scenarios of possible collisions. In this example, this message is located in the look-up table with the scenario in which the bone tracker virtual object 46' has collided with the virtual field-of-view boundary 113. More detailed instructions are also possible based on an avoidance or repulsion vector that defines the direction to be taken to avoid or reverse the collision. The instructions may be to "move the tibia" with an arrow B further displayed or flashing on the displays 28, 29 wherein the arrow B is in the direction of the avoidance or repulsion vector.

The feedback generator 122 may also cause the displays 28, 29 to display a message to the user including instructions to reposition the localizer 34 in response to detecting the collision. For instance, if one of the bone tracker or tool tracker virtual objects 44', 46', 48' was found to have collided with the virtual field-of-view boundary 113, the navigation processor 52 may cause the displays 28, 29 to display a message to the user to "move the camera unit." The particular message may be stored in a look-up table of messages that are associated with particular scenarios of possible collisions. In this example, this message is located in the look-up table with the scenario in which one of the bone tracker or tool tracker virtual objects 44', 46', 48' has collided with the virtual field-of-view boundary 113.

The feedback generator 122 may also cause the displays 28, 29 to display a message to the user including instructions to reposition the manipulator 56 in response to detecting the collision. For instance, if the tool tracker virtual object 48' was found to have collided with the virtual field-of-view boundary 113, the navigation processor 52 may cause the displays 28, 29 to display a message to the user to "move the manipulator." The particular message may be stored in a look-up table of messages that are associated with particular scenarios of possible collisions. In this example, this message is located in the look-up table with the scenario in which the tool tracker virtual object 48' has collided with the virtual field-of-view boundary 113. One reason this feedback may be used is in situations in which the surgical tool 22 cannot otherwise be manipulated to avoid the collision. Additionally, the manipulator 56 has a limited range of motion and if the manipulator 56 is within a predefined threshold of that limited range, this message may be needed to regain additional range of motion during the surgical procedure to avoid collisions.

In addition, the feedback generator 122 may cause the user to experience vibration feedback in the form of vibrations. For instance, when the user is positioning the surgical tool 22 in a manual mode in which the user is grasping a handle of the surgical tool 22, the vibration device 126 may be actuated if the tool tracker virtual object 48' is colliding with or about to collide with the virtual field-of-view boundary 113. The vibration feedback indicates to the user that the tool tracker 48 may be close to moving out of the field-of-view of the localizer 34 thereby allowing the user to cease further motion and prevent the tool tracker 48 from traveling outside the field-of-view. The user can then determine an alternate course.

In one embodiment, the feedback generator 122 provides haptic feedback to the user by responding to a collision with a feedback force that avoids or repulses the collision. The feedback force is determined by the collision detector 120. The feedback force may have force and/or torque components including up to three components of force along x, y, and z axes, and three components of torque about these axes.

In one example, the feedback generator 122 provides the haptic feedback to the user through the surgical tool 22 when the manipulator 56 is operated in the manual mode. This prevents the manipulator 56 from positioning the tool tracker virtual object 48' into the virtual field-of-view boundary 113 thereby avoiding movement of the tool tracker 48 outside of the field-of-view. In one embodiment, the collision detector 120 detects the collision by predicting whether a virtual collision will occur if the manipulator 56 moves the surgical tool 22 to a commanded pose, but before the manipulator controller 54 actually moves the surgical tool 22 to the commanded pose. If a virtual collision is predicted, then the manipulator 56 is controlled to move the surgical tool 22 to an altered commanded pose to avoid the collision.

In some embodiments, the manipulator 56 is a passive manipulator. In this case, the haptic feedback provides feedback to the user after a virtual collision occurs to prevent any further penetration of the tool tracker virtual object 48' into the virtual field-of-view boundary 113 or to reverse the collision. Thus, the collision detection may be responsive to an actual virtual collision or a predicted virtual collision. The feedback generator 122 thus ensures that the manual mode positioning of the surgical tool 22 is controlled so that the tool tracker virtual object 48' stays within, or only penetrates so far into, the virtual field-of-view boundary 113 to prevent the tool tracker 48 from moving outside of the field-of-view of the localizer 34.

When the virtual field-of-view boundary 113 is represented by a polygonal surface such as a mesh, the collision detector 120 can detect collisions in the same manner described above with respect to the tool virtual object 22' and FIG. 10.

The feedback generator 122 can also determine a feedback force to be applied to the surgical tool 22 to stop the unwanted progression of the tool tracker 48 beyond the virtual field-of-view boundary 113 in the same manner described above. In this case, the tool tracker virtual boundary 48' is fixed in relation to the tool virtual boundary 22'. Thus, movement of the tool tracker virtual boundary 48' is controlled by controlling movement of the surgical tool 22 and its virtual boundary 22' as previously described.

During operation of the material removal system 10 in a surgical procedure, the navigation system 20 continuously tracks the position and orientation of each of the virtual objects 44', 46', 48', 22' for purposes of determining whether any of the physical objects associated with these virtual objects 44', 46', 48', 22' pose a risk of causing a line-of-sight obstruction between one of the trackers 44, 46, 48 and the localizer 34. The navigation system 20 also continuously trackers the position and orientation of each of the virtual objects 44', 46', 48' for purposes of determining whether any of the trackers 44, 46, 48 associated with these virtual objects 44', 46', 48' pose a risk of moving outside of the field-of-view of the localizer 34. The purpose being to reduce tracking interruptions so that operation of the manipulator 56 can continue without unnecessary delays caused by losing line-of-sight or by moving outside of the field-of-view. One exemplary method is outlined below.

Figure 12:
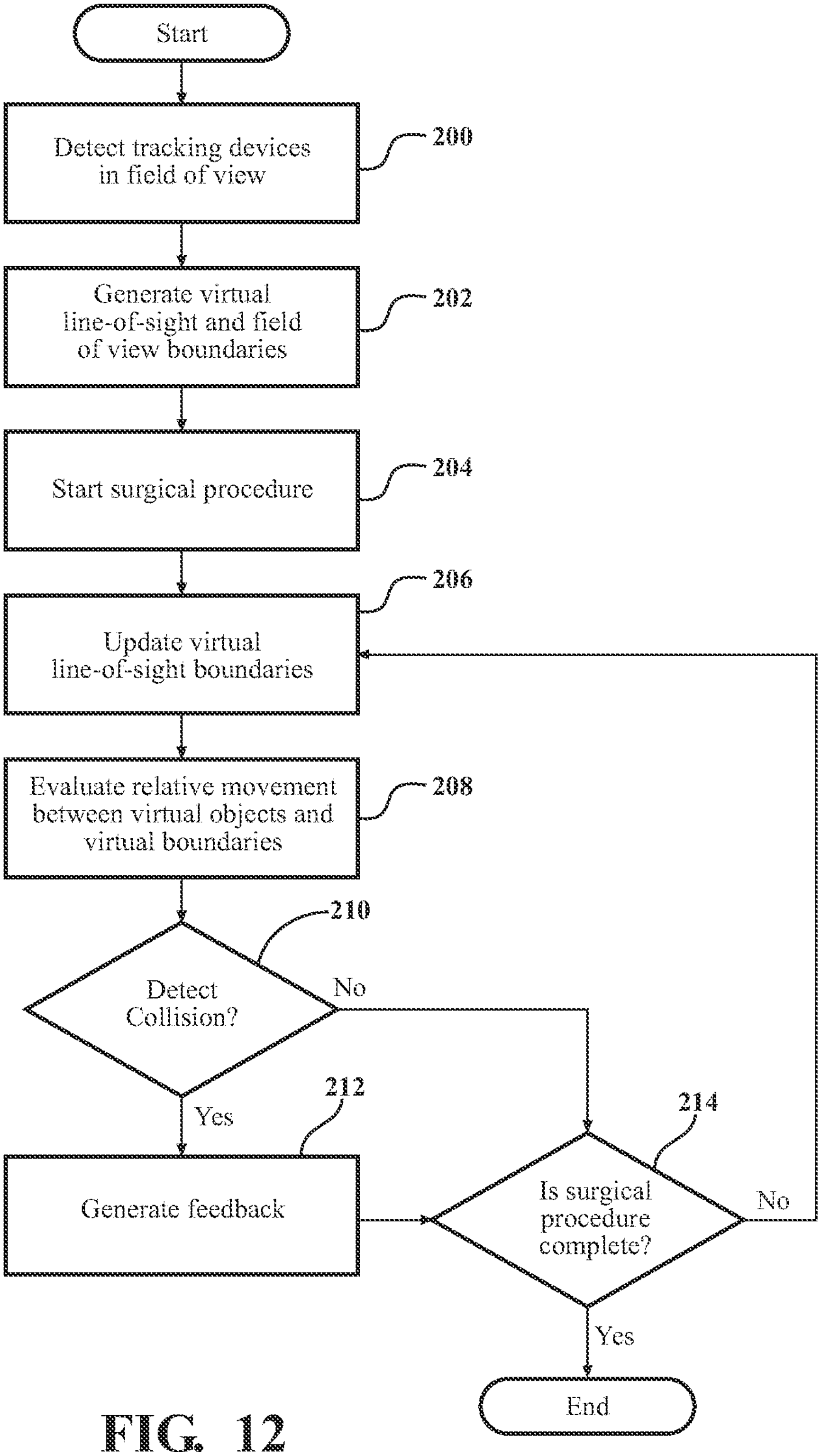
FIG. 12 is a flow chart of steps carried out in one method.

Referring to the flow chart of FIG. 12, in a step 200, the navigation system 20 first detects each of the tracking devices 44, 46, 48 within the field-of-view of the localizer 34. Once the tracking devices 44, 46, 48 are detected, in step 202 the virtual boundary generator 104 generates the virtual line-of-sight boundaries 106, 108, 110 based on the line-of-sight relationships between the tracking devices 44, 46, 48 and the localizer 34. The virtual boundary generator 104 also generates the virtual field-of-view boundary 113 based on the field-of-view of the localizer 34.

The surgical procedure begins in step 204 once the initial virtual boundaries 106, 108, 110, 113 have been generated.

In step 206, the virtual line-of-sight boundaries 106, 108, 110 are updated to account for relative movement between the trackers 44, 46, 48 and the localizer 34 during the surgical procedure.

The virtual objects 44', 46', 48', 22' are preoperatively associated with the physical objects being tracked in the field-of-view of the localizer 34. These are the physical objects that pose a threat of creating a line-of-sight obstruction. Additionally, the bone tracker and tool tracker virtual objects 44', 46', 48' are associated with the trackers 44, 46, 48 that are to be kept in the field-of-view of the localizer 34.

The virtual objects 44', 46', 48', 22' are created and then stored in memory in the navigation computer 26 or the manipulator controller 54, or both, with their parameters being defined relative to the particular coordinate system of their associated tracker 44, 46, 48. For instance, the bone tracker virtual object 44' which represents the structure of the bone tracker 44 attached to the femur F, is created preoperatively and mapped to the bone tracker coordinate system BTRK1 so that the localizer 34 is able to track the bone tracker virtual object 44' by tracking the bone tracker 44, and then transform the parameters defining the bone tracker virtual object 44' into the localizer coordinate system LCLZ.

The collision detector 120 evaluates the relative movement between the virtual objects 44', 46', 48', 22' and the virtual boundaries 106, 108, 110, 113 in step 208. Evaluating movement of the virtual objects 44', 46', 48', 22' may include tracking the position and orientation of each of the virtual objects 44', 46', 48', 22' with respect to a position and orientation of the virtual boundaries 106, 108, 110, 113 to facilitate detection of collisions between the virtual objects 44', 46', 48', 22' and the virtual boundaries 106, 108, 110, 113. Decision block 210 determines whether the collision detector 120 detected a collision between one or more of the virtual objects 44', 46', 48', 22' and one or more of the virtual boundaries 106, 108, 110, 113 (either an actual virtual collision or a predicted virtual collision). If a collision is not detected, then the process flows to decision block 214 to determine whether the surgical procedure is complete. If the surgical procedure is not yet complete, then the process loops back to step 206 and the position and/or orientation of the virtual line-of-sight boundaries 106, 108, 110 is updated (and the virtual field-of-view boundary 113 is updated if the localizer 34 has been moved). If the surgical procedure is complete, then collision detection ends.

Referring back to decision block 210, if a collision is detected, then feedback is generated in step 212. The feedback is in the form of one or more of the audible feedback, visual feedback, vibration feedback, or haptic feedback, as previously described. In particular, the feedback generator 122 instructs the navigation processor 52 or the manipulator controller 54 to activate the annunciator 124, manipulate the displays 28, 29, activate the vibration device 126, and/or generate haptic feedback through the manipulator 56.

Once the feedback is generated, the navigation processor 52 or manipulator controller 54 determines if the surgical procedure is complete in decision block 214. If so, the procedure ends. If not, the process loops again to step 206 to repeat until the surgical procedure is complete. The process loop between subsequent updates to the virtual line-of-sight boundaries 106, 108, 110 in step 206 may occur every time frame in which a commanded position is generated for the manipulator 56 or each time the localizer 34 detects a new position and/or orientation of the trackers 44, 46, 48.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of operating a surgical system comprising a navigation system including a localizer including a field-of-view and a tracker, and one or more controllers coupled to the navigation system, wherein the one or more controllers include a processor, the processor implementing a virtual boundary generator, a collision detector, and a feedback generator, the method comprising:

detecting, with navigation system, the tracker within the field-of-view of the localizer by establishing a line-of-sight relationship between the tracker and the localizer;

generating, with the virtual boundary generator, a virtual line-of-sight boundary based on the line-of-sight relationship;

associating, with the one or more controllers, a virtual object with a physical object;

detecting, with the collision detector, a virtual collision between the virtual object and the virtual line-of-sight boundary; and enabling, with the feedback generator, a response based on detecting the virtual collision.

2. The method of claim 1, comprising the one or more controllers detecting, with the collision detector, the virtual collision between the virtual object and the virtual line-of-sight boundary by:

monitoring, over a plurality of time frames, movement of the virtual object relative to the virtual line-of-sight boundary; and determining, at one or more of the time frames, that a geometric feature of the virtual object causes the virtual collision by meeting or exceeding a threshold distance to the virtual line-of-sight boundary.

3. The method of claim 1, wherein enabling, with the feedback generator, the response comprises the one or more controllers indicating, on a display device, presence of the virtual collision.

4. The method of claim 1, wherein enabling, with the feedback generator, the response comprises the one or more controllers providing, on a display device, an instruction to eliminate presence of the virtual collision.

5. The method of claim 1, wherein enabling, with the feedback generator, the response comprises the one or more controllers generating one or more of: audible, visual, vibrational, or haptic feedback.

6. The method of claim 1, wherein enabling, with the feedback generator, the response comprises the one or more controllers:

commanding a change in position of the physical object to eliminate presence of the virtual collision; or constraining movement of the physical object to eliminate presence of the virtual collision.

7. A method of operating a surgical system comprising a navigation system including a localizer including a field-of-view and a tracker, and one or more controllers coupled to the navigation system, wherein the one or more controllers include a processor, the processor implementing a virtual boundary generator, a collision detector, and a feedback generator, the method comprising:

detecting, with navigation system, the tracker within the field-of-view of the localizer;

generating, with the virtual boundary generator, a virtual field-of-view boundary based on the field-of-view of the localizer;

associating, with the one or more controllers, a virtual object with the tracker;

detecting, with the collision detector, a virtual collision between the virtual object and the virtual field-of-view boundary; and enabling, with the feedback generator, a response based on detecting the virtual collision.

8. The method of claim 7, comprising the one or more controllers detecting, with the collision detector, the virtual collision between the virtual object and the virtual field-of-view boundary by:

monitoring, over a plurality of time frames, movement of the virtual object relative to the virtual field-of-view boundary; and determining, at one or more of the time frames, that a geometric feature of the virtual object causes the virtual collision by meeting or exceeding a threshold distance to the virtual field-of-view boundary.

9. The method of claim 7, wherein enabling, with the feedback generator, the response comprises the one or more controllers indicating, on a display device, presence of the virtual collision.

10. The method of claim 7, wherein enabling, with the feedback generator, the response comprises the one or more controllers providing, on a display device, an instruction to eliminate presence of the virtual collision.

11. The method of claim 7, wherein enabling, with the feedback generator, the response comprises the one or more controllers generating one or more of: audible, visual, vibrational, or haptic feedback.

12. The method of claim 7, wherein the tracker is coupled to a physical object, and wherein enabling, with the feedback generator, the response comprises the one or more controllers:

commanding a change in position of the physical object to eliminate presence of the virtual collision; or constraining movement of the physical object to eliminate presence of the virtual collision.

13. A surgical system comprising:

a navigation system including a localizer including a field-of-view and a tracker; and one or more controllers coupled to the navigation system, wherein the one or more controllers include a processor, the processor implementing a virtual boundary generator, a collision detector, and a feedback generator, and wherein the one or more controllers are configured to:

detect, with navigation system, the tracker within the field-of-view of the localizer with a line-of-sight relationship between the tracker and the localizer;

generate, with the virtual boundary generator, a virtual line-of-sight boundary based on the line-of-sight relationship;

associate a virtual object with a physical object;

detect, with the collision detector, a virtual collision between the virtual object and the virtual line-of-sight boundary; and enable, with the feedback generator, a response based on detection of the virtual collision.

14. The surgical system of claim 13, wherein the one or more controllers detect, with the collision detector, the virtual collision between the virtual object and the virtual line-of-sight boundary by further being configured to:

monitor, over a plurality of time frames, movement of the virtual object relative to the virtual line-of-sight boundary; and determine, at one or more of the time frames, that a geometric feature of the virtual object causes the virtual collision by meeting or exceeding a threshold distance to the virtual line-of-sight boundary.

15. The surgical system of claim 13, further comprising a display device coupled to the one or more controllers, wherein the one or more controllers enable, with the feedback generator, the response by being configured to indicate, on the display device, presence of the virtual collision.

16. The surgical system of claim 13, further comprising a display device coupled to the one or more controllers, wherein the one or more controllers enable, with the feedback generator, the response by being configured to provide, on the display device, an instruction to eliminate presence of the virtual collision.

17. The surgical system of claim 13, wherein the one or more controllers enable, with the feedback generator, the response by being configured to generate one or more of: audible, visual, vibrational, or haptic feedback.

18. The surgical system of claim 13, wherein the one or more controllers enable, with the feedback generator, the response by being configured to:

command a change in position of the physical object to eliminate presence of the virtual collision; or constrain movement of the physical object to eliminate presence of the virtual collision.

19. A surgical system comprising:

a navigation system including a localizer including a field-of-view and a tracker; and one or more controllers coupled to the navigation system, wherein the one or more controllers include a processor, the processor implementing a virtual boundary generator, a collision detector, and a feedback generator, and wherein the one or more controllers are configured to:

detect, with navigation system, the tracker within the field-of-view of the localizer;

generate, with the virtual boundary generator, a virtual field-of-view boundary based on the field-of-view of the localizer;

associate a virtual object with the tracker;

detect, with the collision detector, a virtual collision between the virtual object and the virtual field-of-view boundary; and enable, with the feedback generator, a response based on detection of the virtual collision.

20. The surgical system of claim 19, wherein the one or more controllers detect, with the collision detector, the virtual collision between the virtual object and the virtual field-of-view boundary by being configured to:

monitor, over a plurality of time frames, movement of the virtual object relative to the virtual field-of-view boundary; and determine, at one or more of the time frames, that a geometric feature of the virtual object causes the virtual collision by meeting or exceeding a threshold distance to the virtual field-of-view boundary.

21. The surgical system of claim 19, further comprising a display device coupled to the one or more controllers, wherein the one or more controllers enable, with the feedback generator, the response by being configured to indicate, on the display device, presence of the virtual collision.

22. The surgical system of claim 19, further comprising a display device coupled to the one or more controllers, wherein the one or more controllers enable, with the feedback generator, the response by being configured to provide, on the display device, an instruction to eliminate presence of the virtual collision.

23. The surgical system of claim 19, wherein the one or more controllers enable, with the feedback generator, the response by being configured to generate one or more of: audible, visual, vibrational, or haptic feedback.

24. The surgical system of claim 19, wherein the tracker is coupled to a physical object, and wherein the one or more controllers enable, with the feedback generator, the response by being configured to:

command a change in position of the physical object to eliminate presence of the virtual collision; or constrain movement of the physical object to eliminate presence of the virtual collision.

* * * * *